US009597138B2

(12) United States Patent
Coffeen et al.

(10) Patent No.: US 9,597,138 B2
(45) Date of Patent: Mar. 21, 2017

(54) MOTORIZED BONE CEMENT MIXING AND DELIVERY SYSTEM WITH AN ENLARGED CONNECTOR FOR CONNECTING TO THE CANNULA THROUGH WHICH THE CEMENT IS INJECTED INTO THE PATIENT

(71) Applicant: Stryker Corporation, Kalamazoo, MI (US)

(72) Inventors: Jared P. Coffeen, Hollister, CA (US); Christopher A. Rossman, Comstock Park, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 460 days.

(21) Appl. No.: 14/076,536

(22) Filed: Nov. 11, 2013

(65) Prior Publication Data
US 2014/0094817 A1    Apr. 3, 2014

Related U.S. Application Data

(60) Division of application No. 13/465,615, filed on May 7, 2012, now abandoned, which is a division of (Continued)

(51) Int. Cl.
*A61B 17/88*    (2006.01)
*B01F 7/20*    (2006.01)
(Continued)

(52) U.S. Cl.
CPC ...... *A61B 17/8822* (2013.01); *A61B 17/8833* (2013.01); *B01F 7/0005* (2013.01);
(Continued)

(58) Field of Classification Search
CPC ............ A61B 17/8822; A61B 17/8833; A61B 2017/8844; A61B 2017/8838;
(Continued)

(56) References Cited

U.S. PATENT DOCUMENTS 3,366,369 A    1/1968  Ravasi
4,721,390 A    1/1988  Lindgren
(Continued)

FOREIGN PATENT DOCUMENTS

WO    2008/045329 A2    4/2008

OTHER PUBLICATIONS

"USPTO ISA Search Report and Written Opinion" for PCT App. No. PCT/US2007/021408, Aug. 2008.

*Primary Examiner* — Charles Cooley

(57) ABSTRACT

A bone cement mixing and delivery system including a mixer, a delivery device, and a flexible extension tube. A connector is attached to a distal end of the flexible tube. The connector includes a housing, a fitting and an enlarged knob. A spindle that extends through the housing connects the fitting to the knob so the fitting rotates with the knob. A cannula is connected to the mixing and delivery system by placing the cannula fitting adjacent the connector fitting. The knob is rotated to result in the like rotation of the connector fitting. This causes the complementary threading on the connector fitting and the cannula fitting to engage.

20 Claims, 24 Drawing Sheets

Related U.S. Application Data application No. 12/961,216, filed on Dec. 6, 2010, now Pat. No. 8,172,456, which is a division of application No. 12/652,295, filed on Jan. 5, 2010, now Pat. No. 7,854,543, which is a continuation of application No. 12/416,171, filed on Apr. 1, 2009, now Pat. No. 7,658,537, which is a continuation of application No. PCT/US2007/021408, filed on Oct. 5, 2007.

(60) Provisional application No. 60/828,509, filed on Oct. 6, 2006, provisional application No. 60/969,173, filed on Aug. 31, 2007.

(51) Int. Cl.

| | | |
|---|---|---|
| *B01F 7/00* | (2006.01) | |
| *B01F 7/18* | (2006.01) | |
| *B01F 15/02* | (2006.01) | |
| B01F 13/06 | (2006.01) | |
| A61F 2/30 | (2006.01) | |
| A61F 2/48 | (2006.01) | |

(52) U.S. Cl.
CPC ...... *B01F 7/00116* (2013.01); *B01F 7/00158* (2013.01); *B01F 7/00275* (2013.01); *B01F 7/18* (2013.01); *B01F 15/027* (2013.01); *B01F 15/0279* (2013.01); A61B 2017/8838 (2013.01); A61B 2017/8844 (2013.01); A61F 2002/3056 (2013.01); A61F 2002/30405 (2013.01); A61F 2002/30523 (2013.01); A61F 2002/30558 (2013.01); A61F 2002/30601 (2013.01); A61F 2002/482 (2013.01); A61F 2220/0025 (2013.01); A61F 2250/0073 (2013.01); A61F 2250/0074 (2013.01); B01F 2215/0029 (2013.01)

(58) Field of Classification Search
CPC .. B01F 15/027; B01F 7/0005; B01F 7/00116; B01F 15/0279; B01F 7/00158; B01F 7/18; B01F 7/00275; B01F 2215/0029; A61F 2002/3056; A61F 2250/0074; A61F 2250/0073; A61F 2002/482; A61F 2002/30558; A61F 2002/30405; A61F 2220/0025; A61F 2002/30601; A61F 2002/30523
USPC ....... 366/139, 184, 189, 194–196, 308, 279, 366/601, 190, 192; 606/92–94; 222/192, 222/236
See application file for complete search history.

(56) References Cited

U.S. PATENT DOCUMENTS

| | | |
|---|---|---|
| 4,854,716 A | 8/1989 | Ziemann et al. |
| 4,889,432 A | 12/1989 | Patterson |
| 4,952,065 A | 8/1990 | Kreuziger |
| 5,044,758 A | 9/1991 | Kurtz |
| 5,193,907 A | 3/1993 | Faccioli et al. |
| 5,505,538 A | 4/1996 | Earle |
| 5,531,519 A | 7/1996 | Earle |
| 5,571,282 A | 11/1996 | Earle |
| 5,860,739 A | 1/1999 | Cannon |
| 5,975,751 A | 11/1999 | Earle |
| 6,042,262 A | 3/2000 | Hajianpour |
| 6,176,607 B1 | 1/2001 | Hajianpour |
| 6,676,664 B1 | 1/2004 | Al-Assir |
| 6,783,515 B1 | 8/2004 | Miller et al. |
| 6,916,308 B2 | 7/2005 | Dixon et al. |
| 7,048,743 B2 | 5/2006 | Miller et al. |
| 7,112,205 B2 * | 9/2006 | Carrison ............ A61B 17/3472 606/92 |
| 7,278,778 B2 | 10/2007 | Sand |
| 7,658,537 B2 * | 2/2010 | Coffeen ............ A61B 17/8833 366/139 |
| 7,841,763 B2 | 11/2010 | Foster |
| 7,854,543 B2 * | 12/2010 | Coffeen ............ A61B 17/8833 366/139 |
| 8,172,456 B2 * | 5/2012 | Coffeen ............ A61B 17/8833 366/139 |
| 8,192,071 B2 | 6/2012 | Wright et al. |
| 8,721,600 B2 * | 5/2014 | Henniges |
| 2004/0193171 A1 | 9/2004 | DiMauro et al. |
| 2004/0204715 A1 | 10/2004 | Evans et al. |
| 2004/0215202 A1 | 10/2004 | Preissman |
| 2004/0260303 A1 * | 12/2004 | Carrison ............ A61B 17/3472 606/92 |
| 2004/0260304 A1 | 12/2004 | Faccioli et al. |
| 2005/0070915 A1 | 3/2005 | Mazzuca et al. |
| 2005/0105385 A1 | 5/2005 | McGill et al. |
| 2005/0113843 A1 | 5/2005 | Arramon |
| 2005/0228397 A1 | 10/2005 | Malandain et al. |
| 2006/0028907 A1 | 2/2006 | Barker et al. |
| 2006/0052794 A1 * | 3/2006 | McGill ............ A61B 17/8816 606/93 |
| 2006/0074433 A1 | 4/2006 | McGill et al. |
| 2006/0133193 A1 | 6/2006 | Arramon |
| 2006/0227653 A1 | 10/2006 | Keller |
| 2007/0211565 A1 | 9/2007 | Plishka et al. |
| 2008/0116224 A1 | 5/2008 | Krueger et al. |
| 2009/0057168 A1 * | 3/2009 | Smit .................. A61B 17/8833 206/221 |
| 2009/0257306 A1 * | 10/2009 | Coffeen ............ A61B 17/8833 366/189 |
| 2010/0014379 A1 | 1/2010 | Wright et al. |
| 2010/0076480 A1 | 3/2010 | Lu et al. |
| 2010/0091606 A1 | 4/2010 | Kwan et al. |
| 2010/0110820 A1 * | 5/2010 | Coffeen ............ A61B 17/8833 366/43 |
| 2011/0194371 A1 * | 8/2011 | Coffeen ............ A61B 17/8833 366/51 |
| 2014/0094817 A1 * | 4/2014 | Coffeen ............ A61B 17/8833 606/94 |
| 2016/0045241 A1 * | 2/2016 | Boboltz ............ A61B 17/8819 606/93 |

* cited by examiner

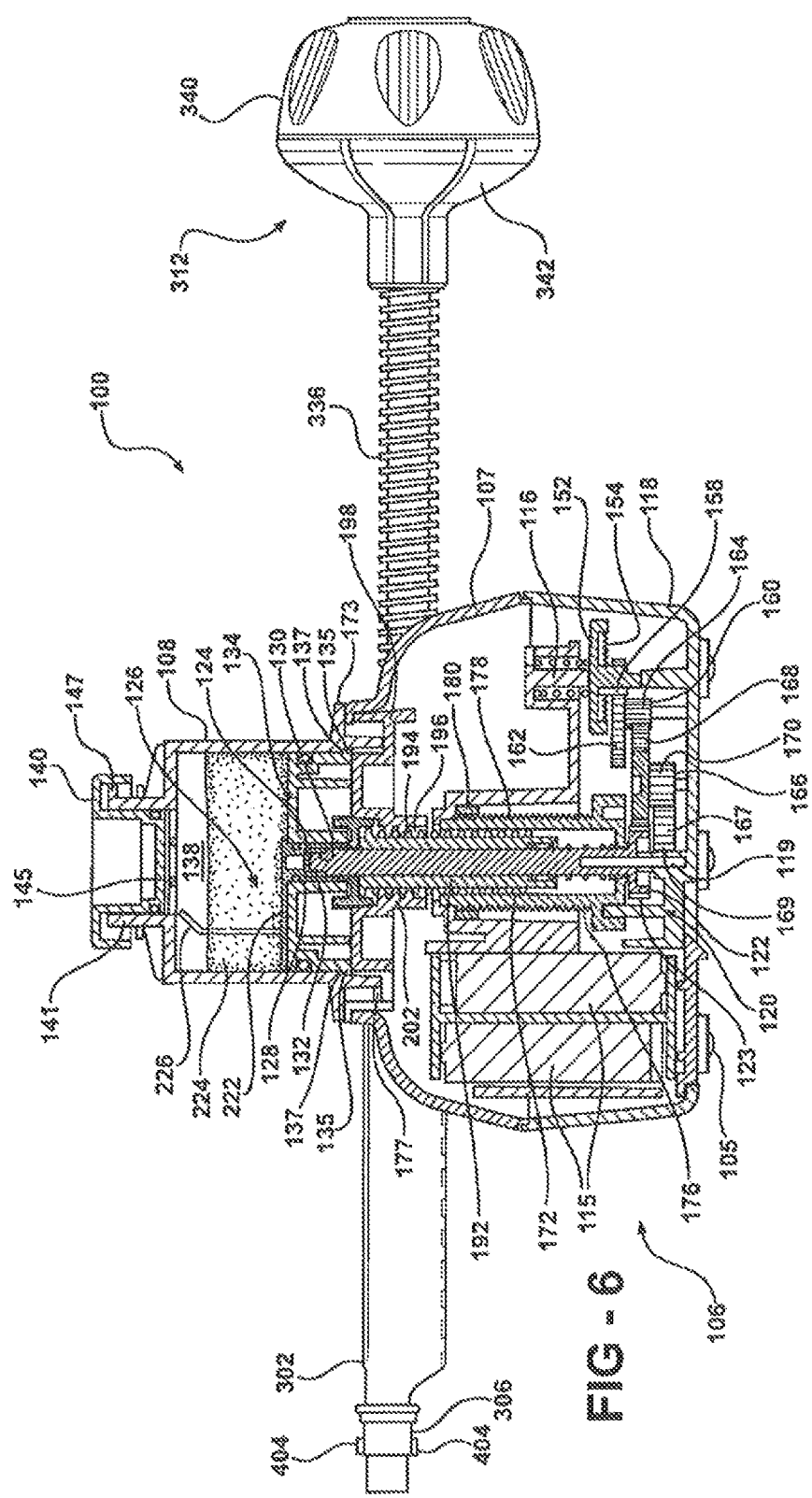

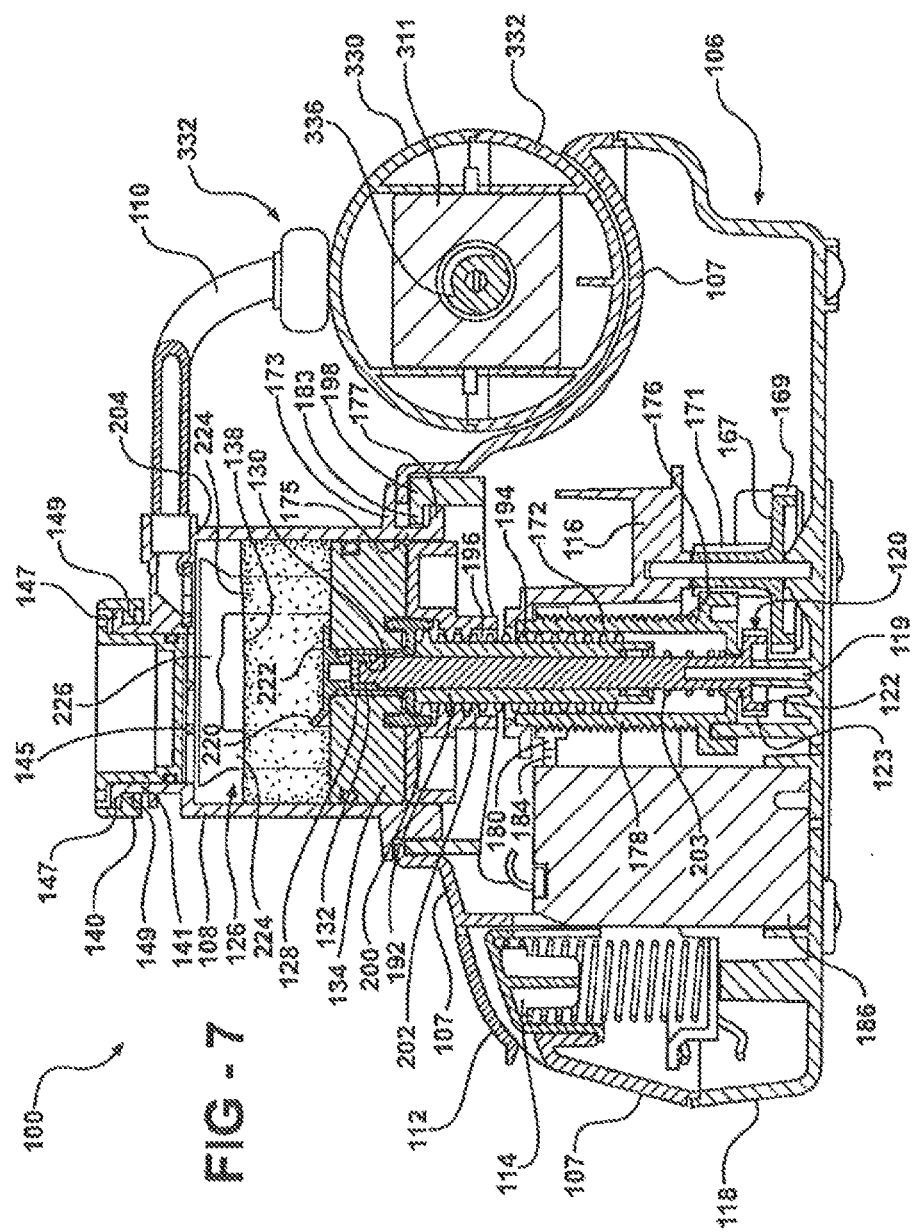

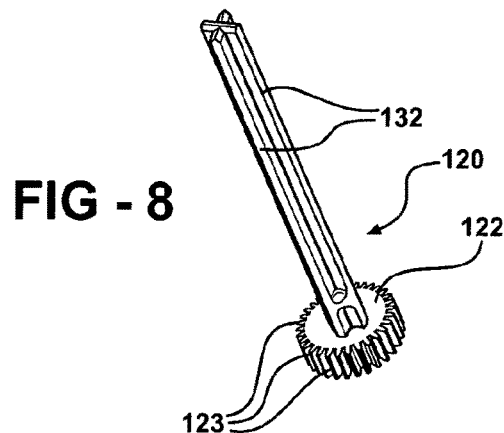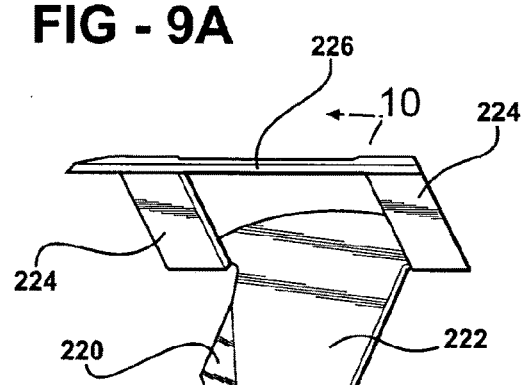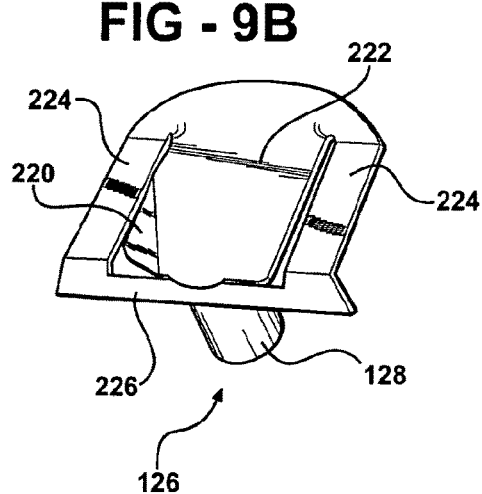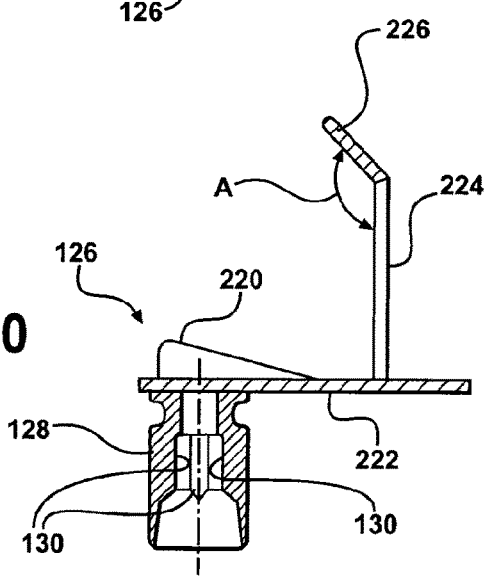

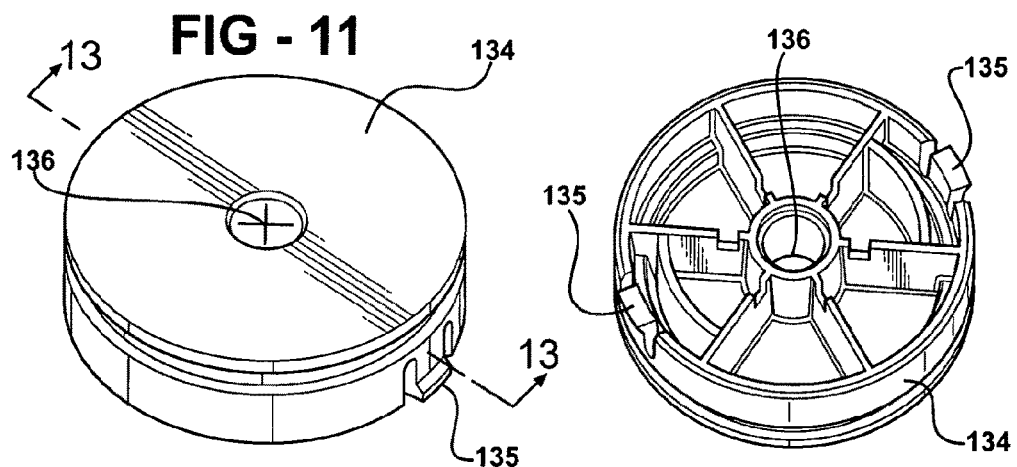
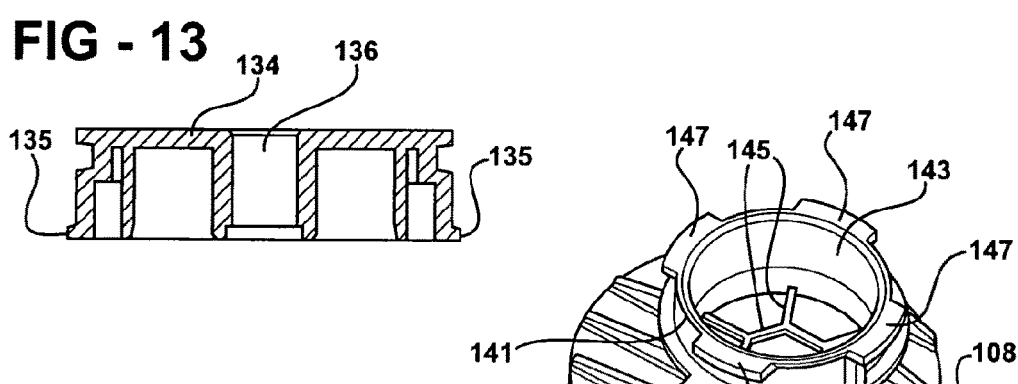
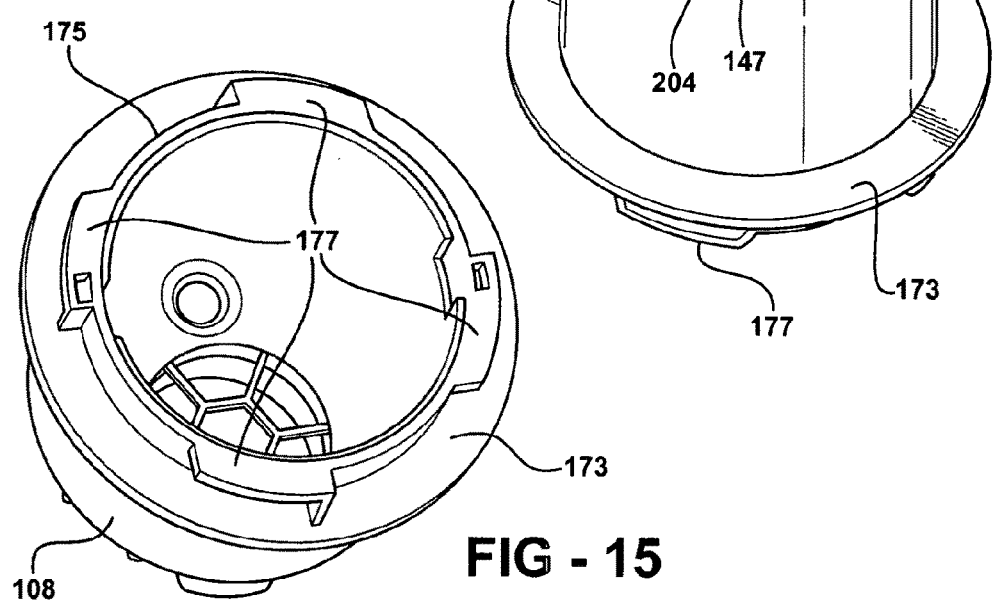

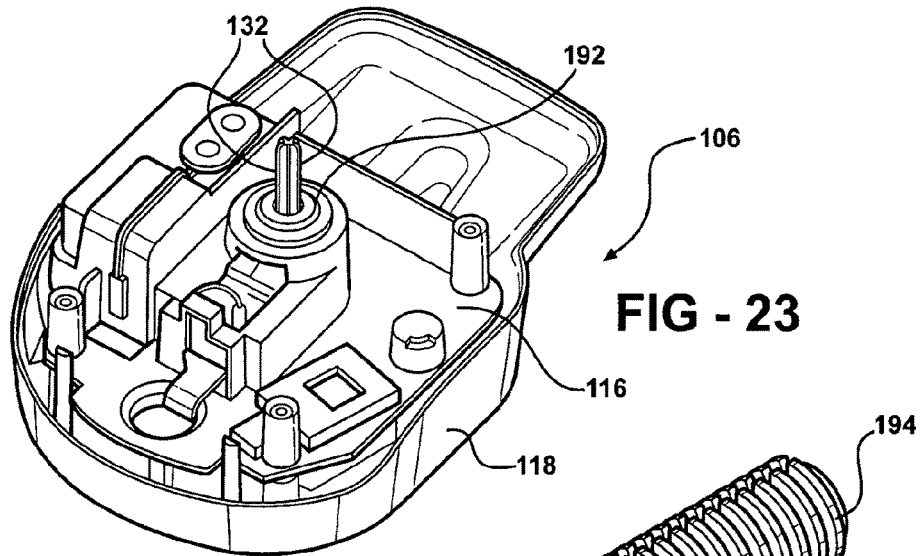
FIG - 23
FIG - 25
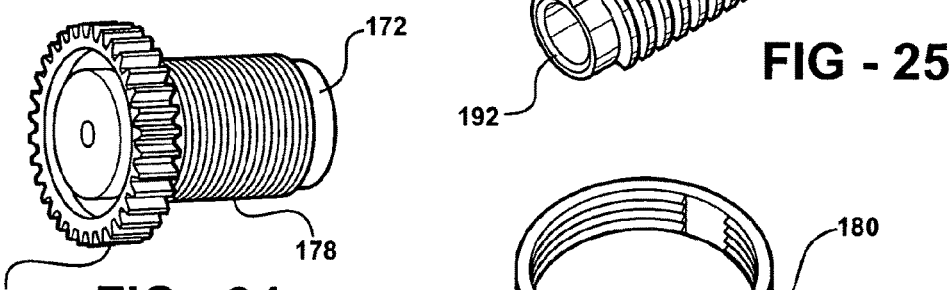
FIG - 24
FIG - 26
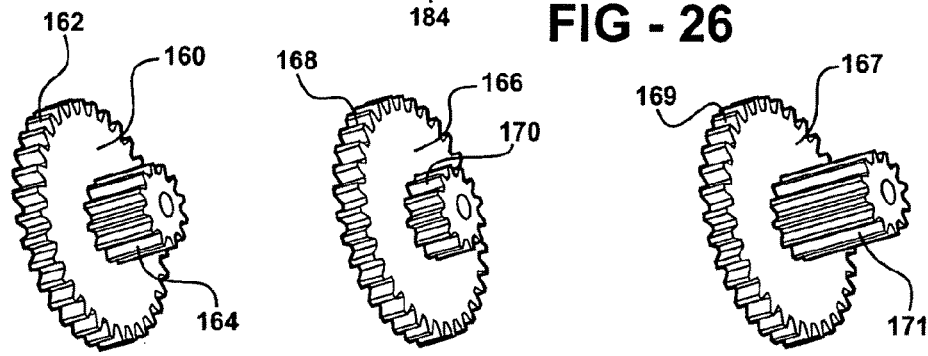
FIG - 27   FIG - 28   FIG - 29

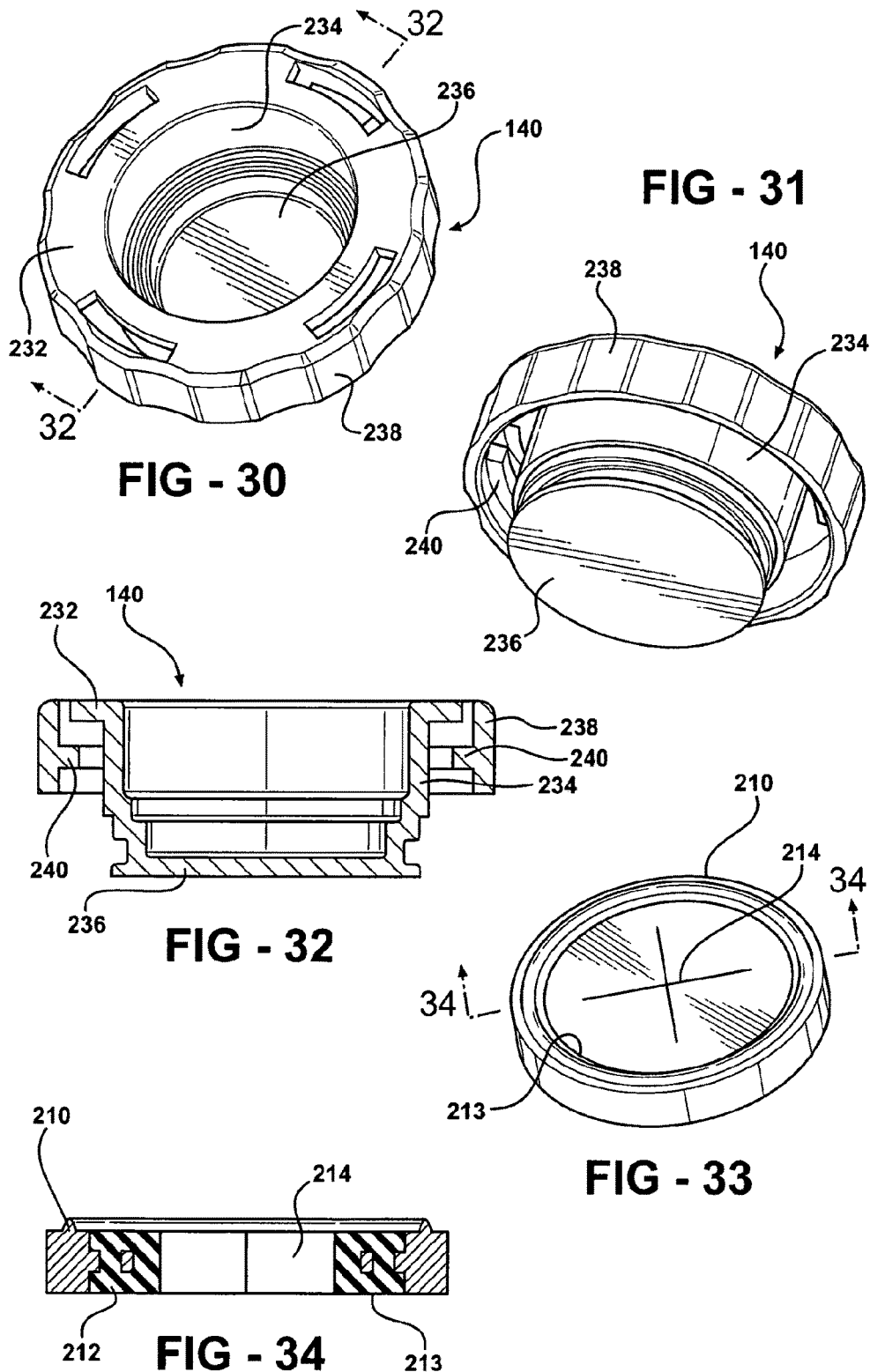

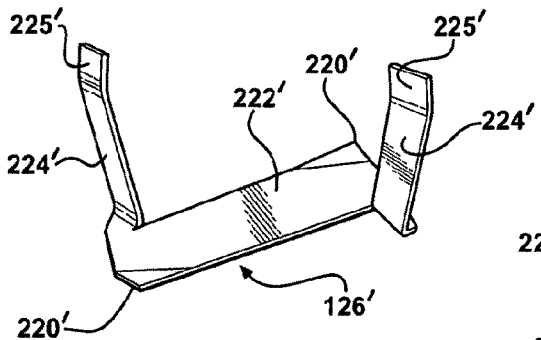
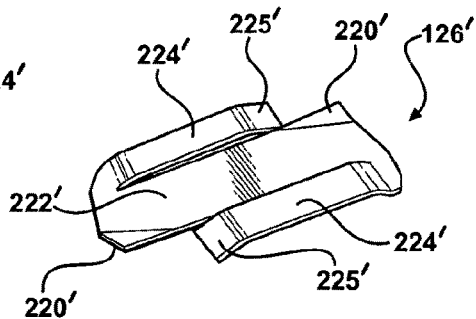
FIG - 35A     FIG - 35B
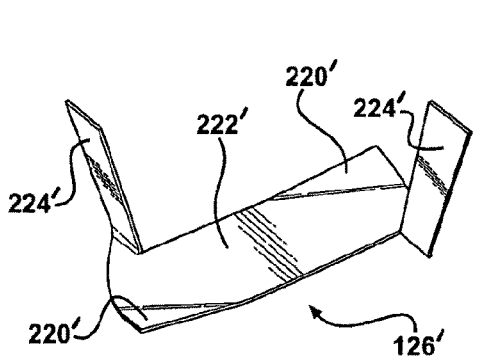
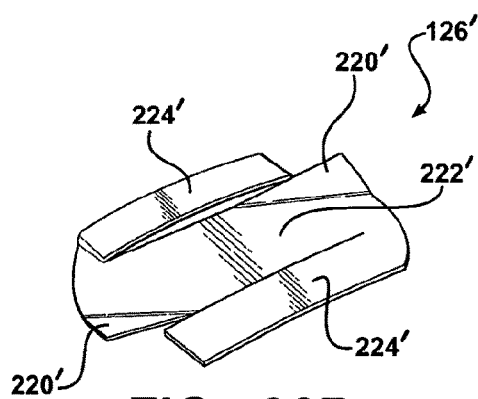
FIG - 36A     FIG - 36B
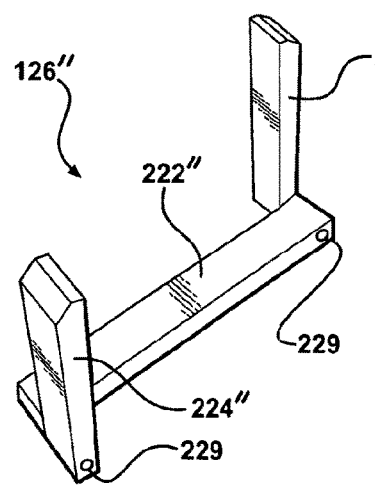
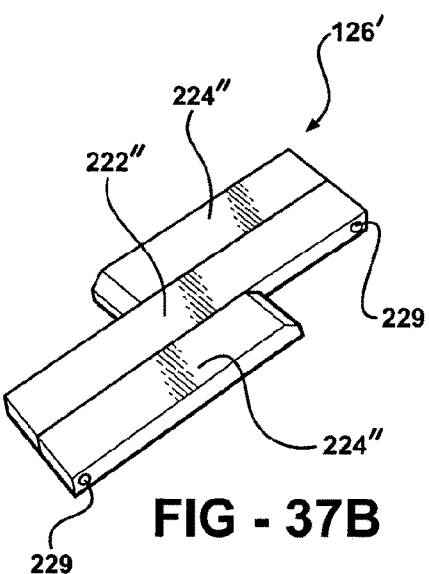
FIG - 37A     FIG - 37B

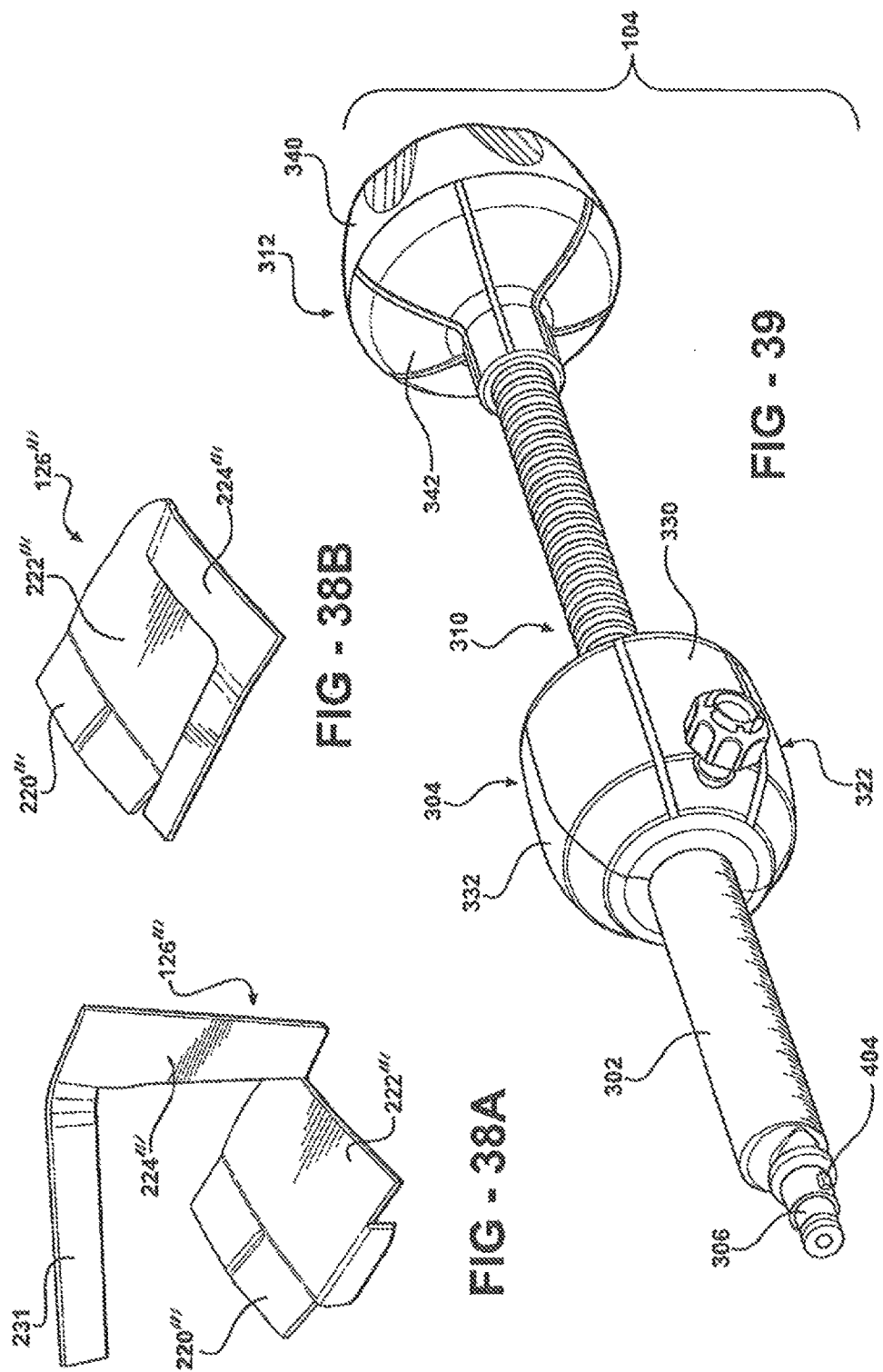

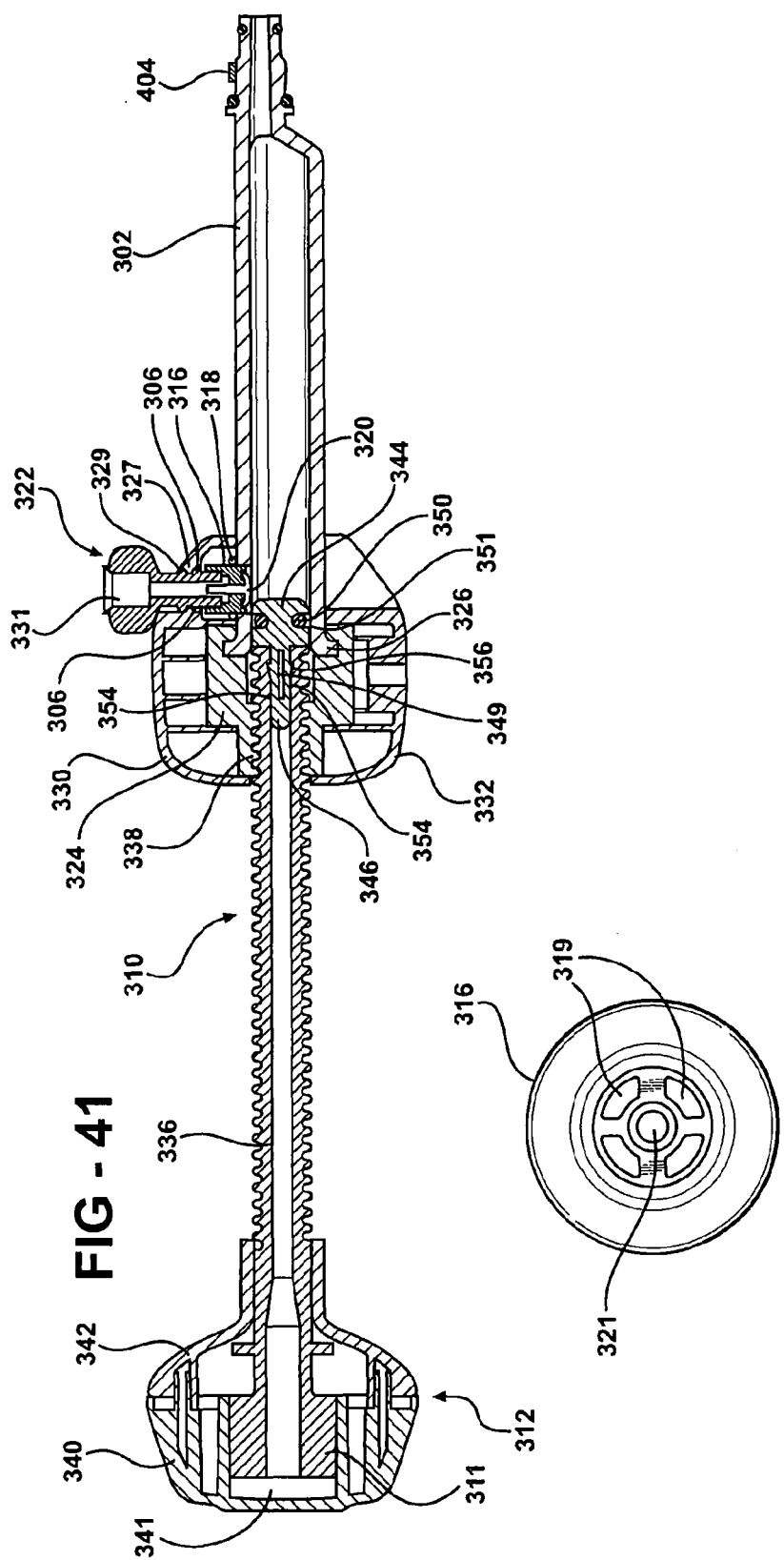

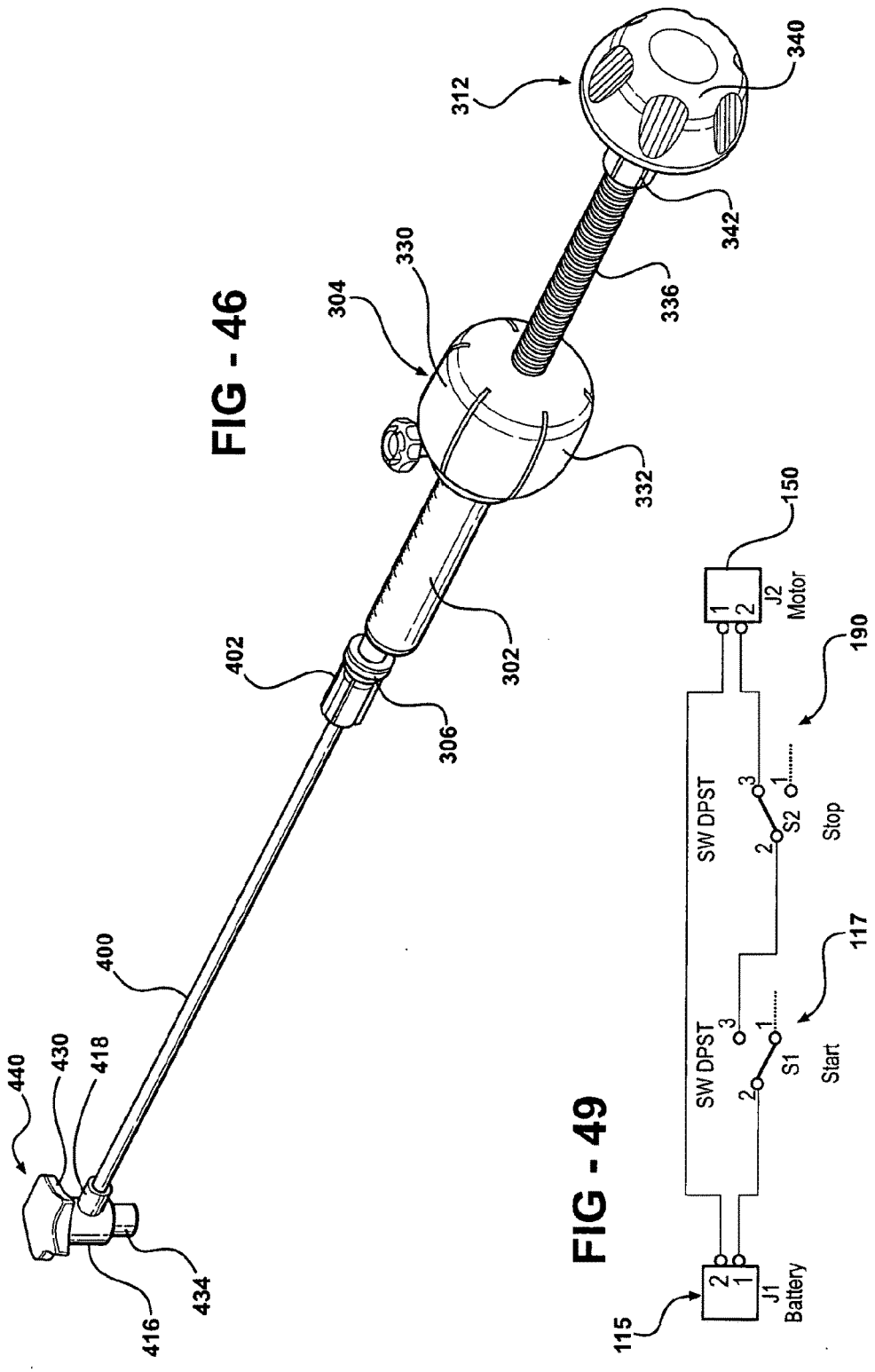

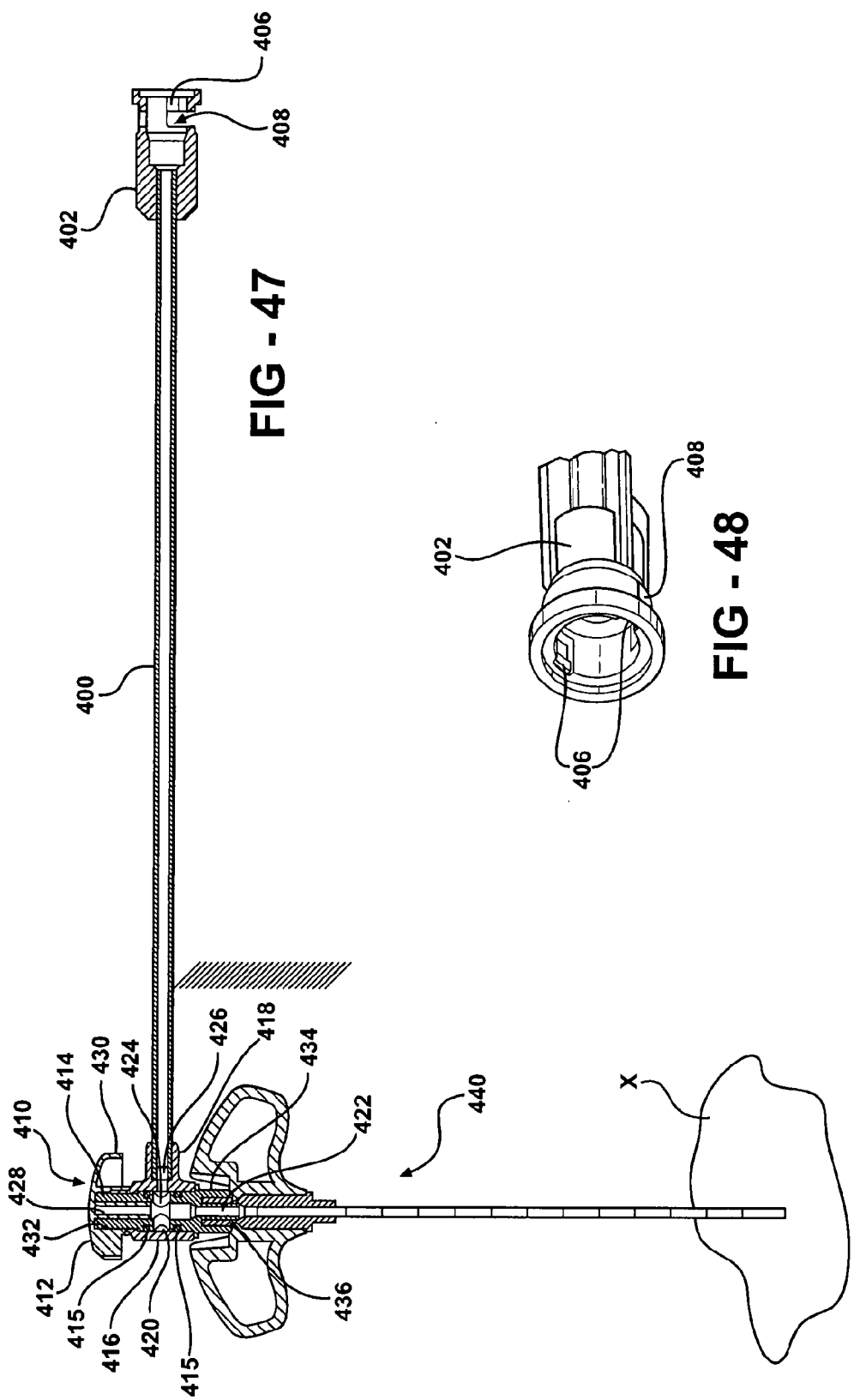

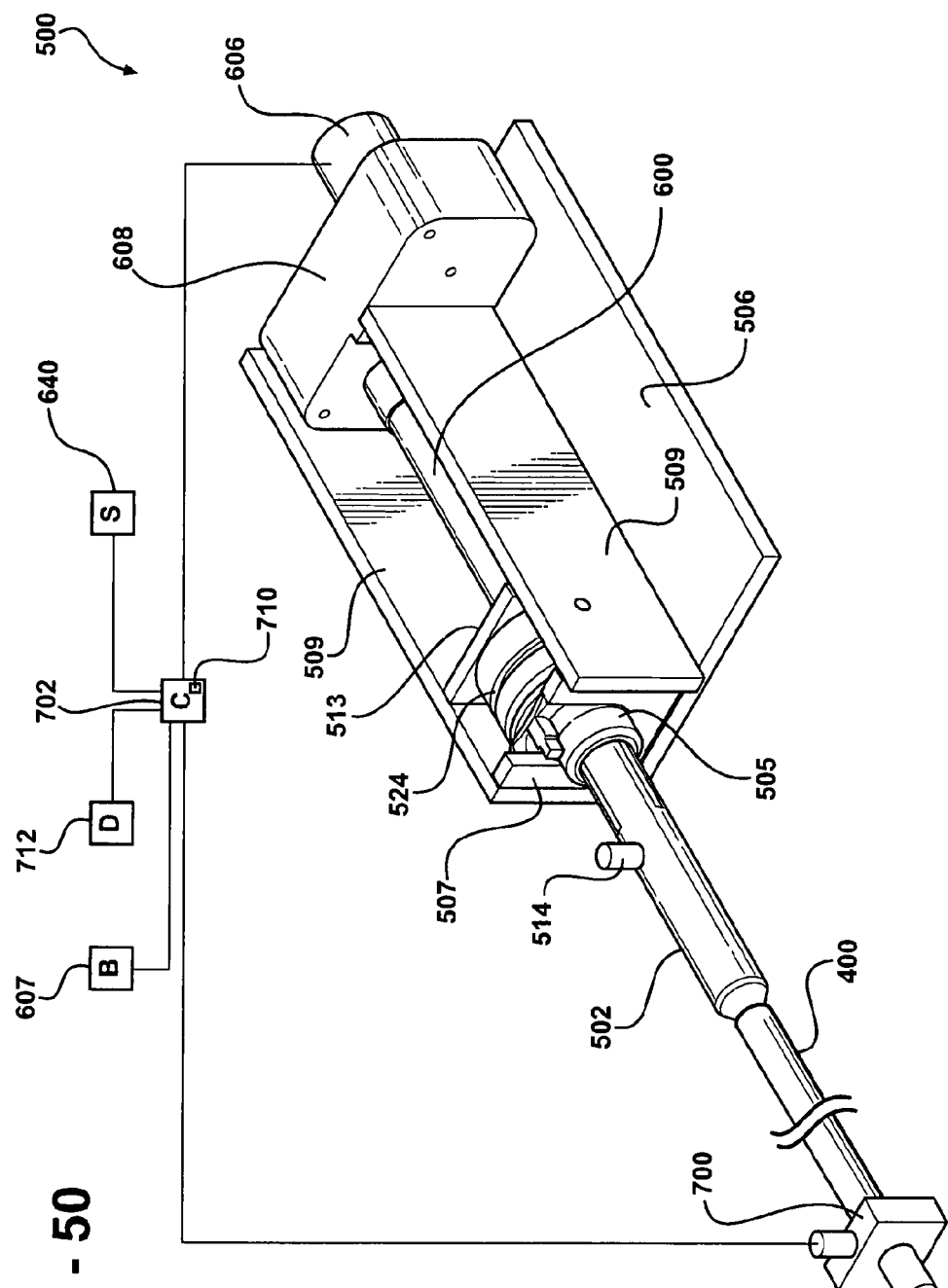

MOTORIZED BONE CEMENT MIXING AND DELIVERY SYSTEM WITH AN ENLARGED CONNECTOR FOR CONNECTING TO THE CANNULA THROUGH WHICH THE CEMENT IS INJECTED INTO THE PATIENT

CROSS-REFERENCE TO RELATED APPLICATIONS

This application is a divisional of U.S. patent application Ser. No. 13/465,615 filed 7 May 2012 now abandoned. Application Ser. No. 13/465,615 is a divisional of U.S. patent application Ser. No. 12/961,216, filed 6 Dec. 2010, now U.S. Pat. No. 8,172,456. Application Ser. No. 12/961,216 is a divisional of U.S. patent application Ser. No. 12/652,295, filed 5 Jan. 2010, now U.S. Pat. No. 7,854,543. Application Ser. No. 12/652,295 is a continuation of U.S. patent application Ser. No. 12/416,171, filed 1 Apr. 2009, now U.S. Pat. No. 7,658,537. Application Ser. No. 12/416,171 is a continuation application of PCT Application No. PCT/US2007/021408, filed 5 Oct. 2007, which claims priority to U.S. Provisional Patent Application Ser. No. 60/828,509, filed 6 Oct. 2006 and U.S. Provisional Patent Application Ser. No. 60/969,173, filed 31 Aug. 2007. Each of the above-listed priority applications are hereby incorporated by reference in their entirety.

FIELD OF INVENTION

The present invention is generally related to bone cement mixing and delivery systems in which separate components of bone cement are mixed together in a mixer to form a bone cement mixture. The mixture is transferred to a delivery device and then delivered to a target site, such as a vertebral body or other anatomical site.

BACKGROUND OF THE INVENTION

Bone cement mixing and delivery systems are well known for mixing separate components of bone cement together to form a uniform bone cement mixture and then delivering that mixture to a target site. Typically, such systems employ a mixer having a handle for manually mixing the components. Once mixed, the mixture is then manually transferred to a delivery device such as a syringe. The syringe is used to inject the mixture into the target site. Examples of target sites include medullary canals for total hip arthroplasty procedures, vertebral bodies for vertebroplasty or kyphoplasty procedures, and other sites in which bone cement is required.

Often, the types of bone cements used in these procedures have short working time windows of only a few minutes thereby affecting the amount of time available for mixing and delivering the mixture to the target site. Current systems require a great deal of user interaction in set-up, including manually mixing the bone cement components and manually transferring the mixture to the delivery device. This user interaction delays delivery of the mixture to the target site, while also exhausting the user's energy. As a result, there is a need for bone cement mixing and delivery systems that are capable of quick set-up, with little user interaction.

One example of a bone cement mixing and delivery system that attempts to improve set-up time is shown in U.S. Pat. No. 5,571,282 to Earle. Earle discloses a motorized mixer that is used to mix the bone cement components. The mixer mixes the components a pre-selected amount of time, as set by the user. At the end of the pre-selected time, the mixer stops automatically and pressure is applied to the mixture to push the mixture out through a port in the bottom of the mixer to a syringe or a delivery cartridge.

The release of odors and gases associated with the bone cement components during mixing can also be undesirable. As a result, there is also a need for bone cement mixing and delivery systems that are substantially self-contained such that the odors and gases associated with the components are not substantially released during mixing or transfer.

One example of a bone cement mixing and delivery system that provides some containment is shown in U.S. Pat. No. 5,193,907 to Faccioli et al. Faccioli et al. discloses an apparatus for mixing and delivering bone cement formed from liquid and powder components. The apparatus comprises a cylindrical body and a plunger slidable within the body. A powder chamber stores the powder component between the plunger and a distal end of the body. A glass ampoule stores the liquid component inside the plunger. To mix the components, a user presses a plug in the plunger's proximal end to urge a tip of the glass ampoule against a cammed surface (or against a piercing member) to release the liquid component. The liquid component then passes through channels defined in the plunger's head to the powder chamber. The liquid and powder are mixed by shaking the body to form the bone cement mixture. After mixing, the plunger is pressed to discharge the bone cement mixture out of an exit port in the body and through a flexible conduit to a target site.

These prior art systems are suitable for reducing set-up times, conserving a user's energy, and reducing exposure of the user to the bone cement components. However, there is still a need in the art for bone cement mixing and delivery systems that are capable of further reducing set-up time and enabling quick operation to deliver bone cement to a target site.

SUMMARY OF THE INVENTION

The present invention provides a bone cement mixing and delivery system. The system comprises a mixer for mixing components to form a bone cement mixture and a delivery device for receiving the bone cement mixture from the mixer and for delivering the mixture to a target site. The mixer includes a housing defining a mixing chamber for receiving the components of bone cement. The delivery device includes a reservoir defining a delivery chamber in communication with the mixing chamber for receiving the mixture from the mixing chamber. The mixer further includes a mixing paddle disposed in the mixing chamber for mixing the components to form the mixture. A mixing shaft engages the mixing paddle. A transfer mechanism transfers the mixture out from the mixing chamber and into the delivery chamber. A motor operatively engages both the mixing shaft and the transfer mechanism. The motor operates to rotate the mixing shaft and mix the components in the mixing chamber for a predetermined mixing time to form the mixture. The motor also operates to actuate the transfer mechanism to automatically transfer the mixture from the mixing chamber to the delivery chamber after the predetermined mixing time has elapsed.

A method of mixing and transferring the components is also provided. The method includes disposing the components in the mixing chamber of the mixer with the mixing paddle. The motor is started to actuate the mixing shaft and move the mixing paddle in the mixing chamber to mix the components for a predetermined mixing time. After the predetermined mixing time elapses, operation of the motor continues to actuate the transfer mechanism. A predetermined amount of the mixture is automatically transferred from the mixing chamber to the delivery chamber after the predetermined mixing time has elapsed and in response to actuating the transfer mechanism.

The system and method of the present invention have the advantage of using the same motor to actuate both the mixing paddle and the transfer mechanism to minimize weight, cost, and waste, especially considering that the system is preferably intended for single use. Furthermore, the system and method of the present invention reduce user interaction compared to prior art devices and increases the readiness in which an operator can prepare a batch of bone cement for surgical purposes. This is useful when the bone cement increases in viscosity quickly and has a short working window.

BRIEF DESCRIPTION OF THE DRAWINGS

These and other objects, features and advantages of this invention will be apparent from the following detailed description of the preferred embodiment and accompanying drawings in which:

FIG. 6 is a cross-sectional view of the system of FIG. 1 in a mixing phase;

FIG. 7 is another cross-sectional view of the system of FIG. 1 in the mixing phase;

FIG. 8 is a perspective view of a mixing shaft of the mixer;

FIG. 9A is a top perspective view of a mixing paddle of the mixer;

FIG. 9B is a top perspective view of the mixing paddle in a flattened state;

FIG. 10 is a cross-sectional view of the mixing paddle taken generally along the line 10-10 in FIG. 9;

FIG. 11 is a top perspective view of a piston of the mixer;

FIG. 12 is a bottom perspective view of the piston;

FIG. 13 is a cross-sectional view of the piston taken generally along the line 13-13 in FIG. 11;

FIG. 14 is a top perspective view of a mixer housing of the mixer;

FIG. 15 is a bottom perspective view of the mixer housing;

FIG. 23 is a top perspective view of the base of the mixer;

FIG. 24 is a perspective view of a transfer gear;

FIG. 25 is a perspective view of a driver;

FIG. 26 is a perspective view of a switch nut;

FIGS. 27-29 are perspective views of various spur gears;

FIG. 30 is a top perspective view of a cap of the mixer;

FIG. 31 is a bottom perspective view of the cap;

FIG. 32 is a cross-sectional view of the cap taken generally along the line 32-32 in FIG. 30;

FIG. 33 is a top perspective view of a valve ring of the mixer;

FIG. 34 is a cross-sectional view of the valve ring taken generally along the line 34-34 in FIG. 32;

FIGS. 35A-38B are top perspective views of alternative mixing paddles in normal and flattened states;

FIG. 39 is a top perspective view of the delivery device;

FIG. 41 is a cross-sectional view of the delivery device;

FIG. 42 is a top view of a valve housing of the delivery device;

FIG. 46 is a top perspective view of the delivery device coupled to an extension tube and an enlarged luer-lock connector;

FIG. 47 is a cross-sectional view of the extension tube and the enlarged luer-lock connector;

FIG. 48 is a perspective view of a lock fitting of the extension tube;

FIG. 49 is an electrical schematic of the mixer;

FIG. 50 is a top perspective view of a motorized delivery device;

DETAILED DESCRIPTION OF THE INVENTION

For the purpose of promoting an understanding of the present invention, references are made in the text hereof to exemplary embodiments of a bone cement mixing and delivery system, only some of which are depicted in the figures. It should nevertheless be understood that no limitations on the scope of the invention are thereby intended. One of ordinary skill in the art will readily appreciate that modifications such as those involving the materials from which the components are made, the size of the components, functional equivalents of the elements, and the inclusion of additional elements do not depart from the spirit and scope of the present invention. Some of these possible modifications are discussed in the following description. Therefore, specific details disclosed herein are not to be interpreted as limiting, but rather as support for the claims and as a representative basis for teaching one skilled in the art to employ the present invention in virtually any appropriately detailed system, structure, or manner.

As used herein, "distal" refers to the end of the delivery device from which the bone cement mixture is discharged, and "proximal" refers to the end of the delivery device away from the end from which the bone cement mixture is discharged. The terms "substantially" and "approximately," as used herein, may be applied to modify any quantitative representation that could permissibly vary without resulting in a change in the basic function to which it is related.

Figure 1:
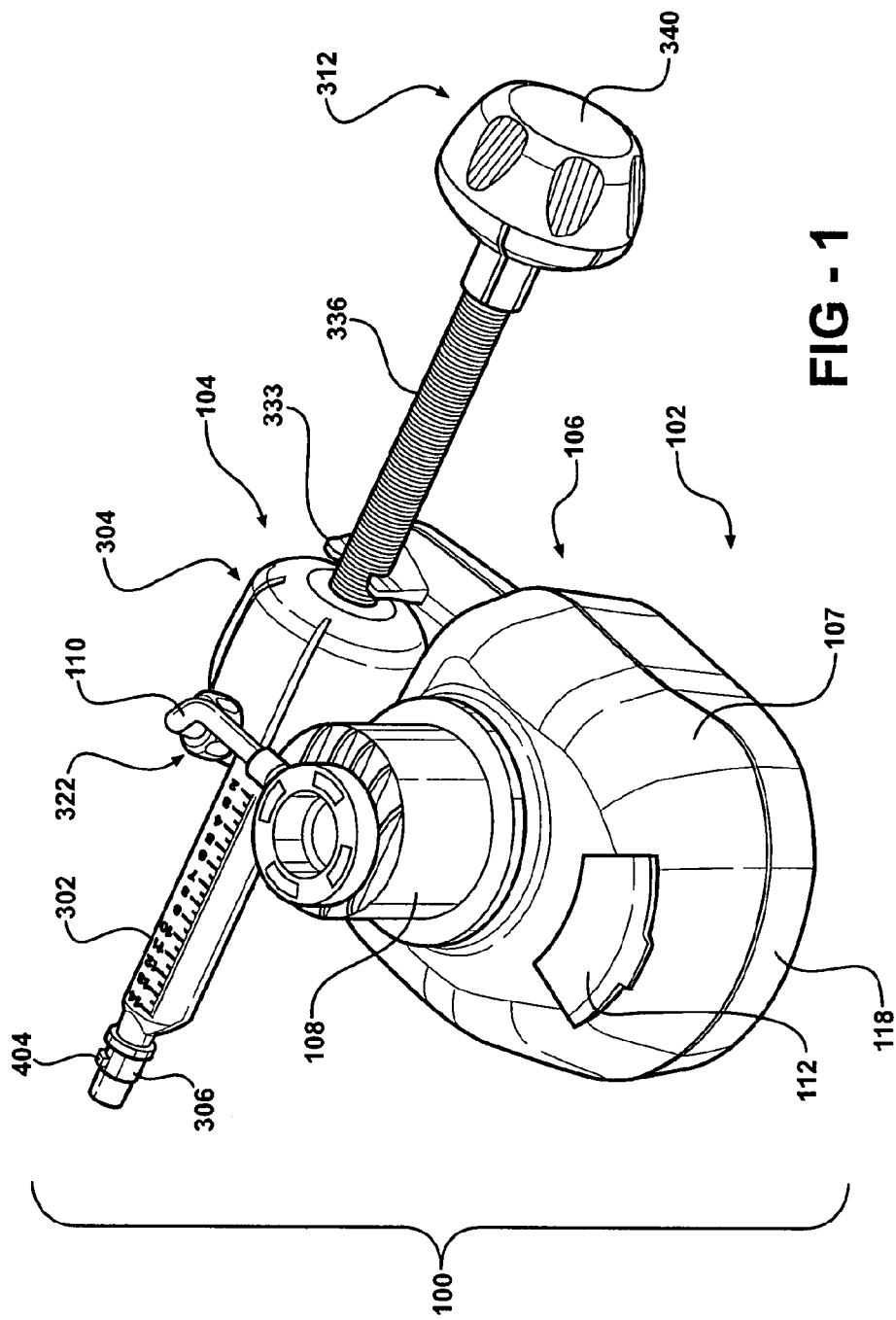
FIG. 1 is a top perspective view of a bone cement mixing and delivery system including a mixer and a delivery device.

Referring in more detail to the drawings, a bone cement mixing and delivery system of the present invention is generally shown at 100 in FIG. 1. The system 100 includes a mixer 102 to mix separate components of bone cement to form a bone cement mixture and a delivery device 104 to deliver the mixture to a target site. The target site may be an anatomical site such as a vertebral body or the target site may be in or near an implant.

The system 100 is useful in any procedure in which bone cement or any other mixture is required, particularly when time is a constraint and exposure of the material or its vapors to the user is to be minimized. The system 100 is capable of mixing the components and automatically transferring the mixture to the delivery device 104 upon completion of mixing with no operator interaction. This reduces variability in mixing between users and creates consistency across multiple users. This automatic transfer feature reduces time and energy otherwise spent by a user to manually mix and transfer the mixture to a delivery device such as a conventional syringe. The system 100 also reduces exposure of the user to the bone cement components during mixing and transfer when compared to conventional mixing and delivery devices.

I. Mixer

Figure 2:
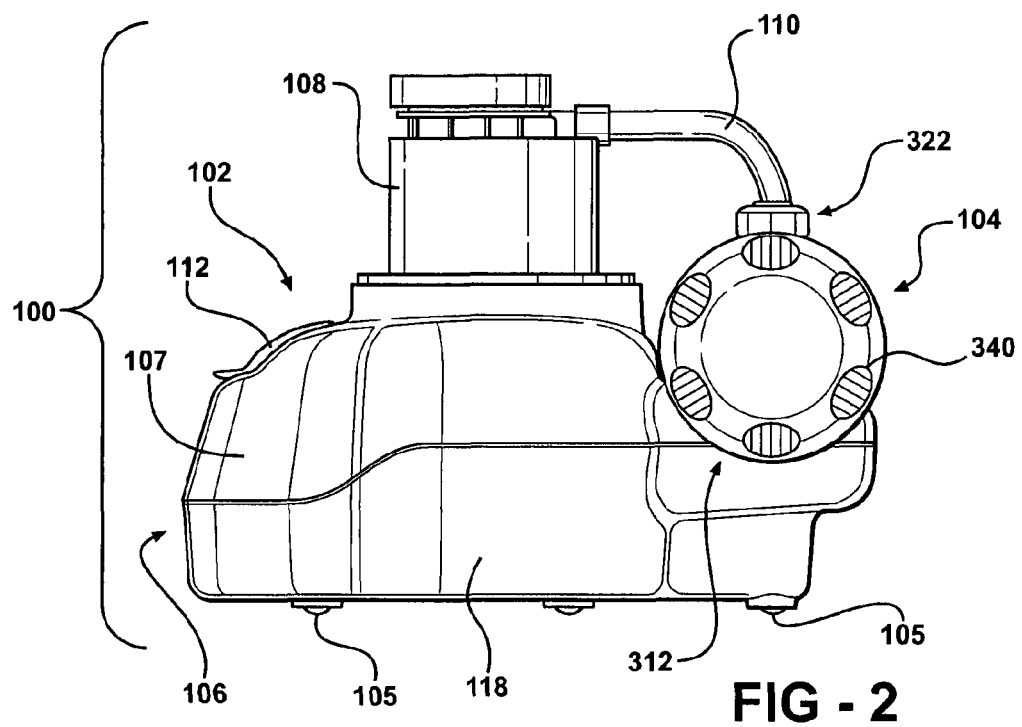
FIG. 2 is a side elevational view of the system of FIG. 1.
Figure 3:
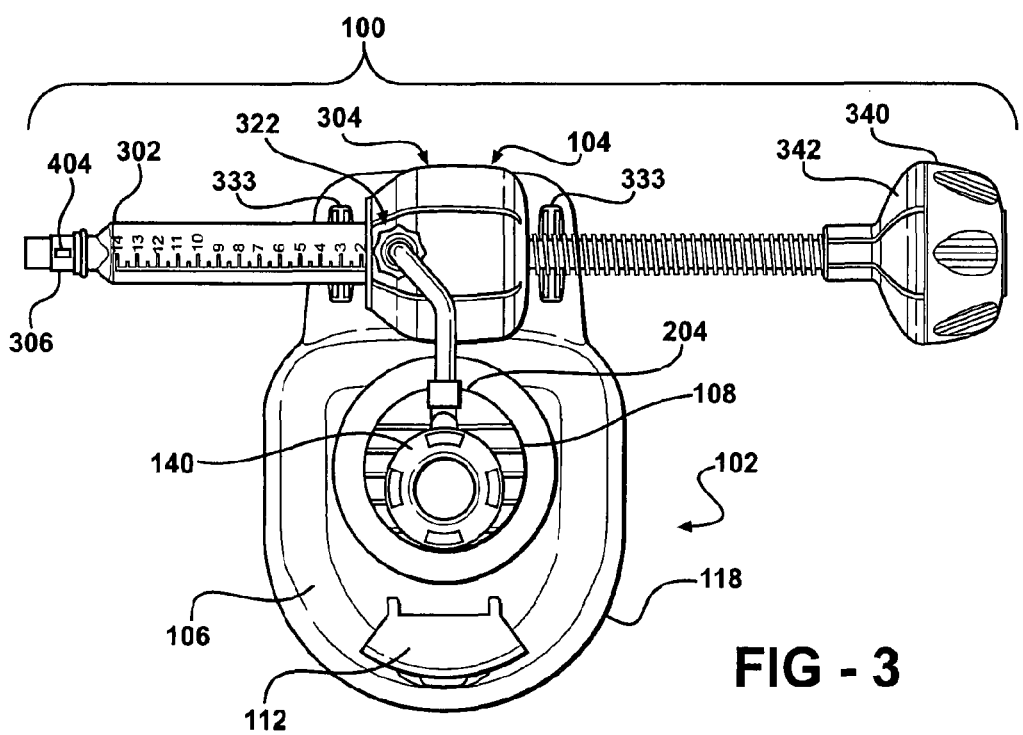
FIG. 3 is a top view of the system of FIG. 1.

Referring to FIGS. 1-3, the mixer 102 includes a base 106 for supporting the mixer 102 on a surface. The base 106 includes rubber feet 105 for gripping the surface. A casing 107 mounts to the base 106 to cover the base and provide an aesthetically pleasing shape to the mixer 102. A mixer housing 108 is coupled to the casing 107. A transfer conduit 110 links the mixer housing 108 to the delivery device 104. The transfer conduit 110 conveys the mixture from the mixer 102 to the delivery device 104. A switch cover 112 is pivotally mounted to the casing 107 to protect a switch button 114 (see FIG. 4) used to begin operation of the mixer 102. Once the switch button 114 is pressed, the bone cement components are mixed together to form the mixture and then, once mixing is complete, the mixture is automatically transferred through the transfer conduit 110 to the delivery device 104.

Figure 4:
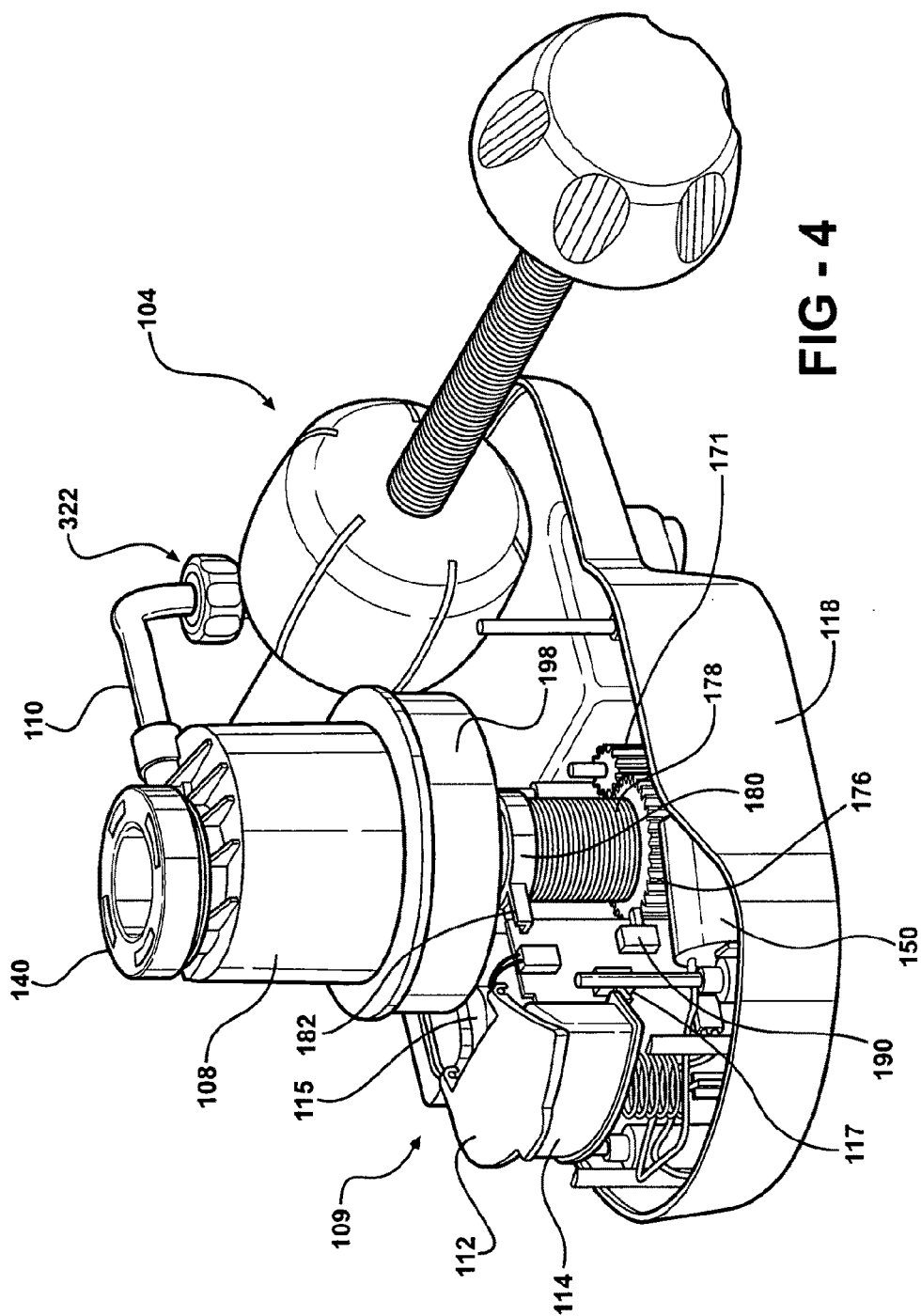
FIG. 4 is a partial front perspective view of the system with a casing and middle housing portion removed to show a motor and transfer mechanism of the mixer.
Figure 5:
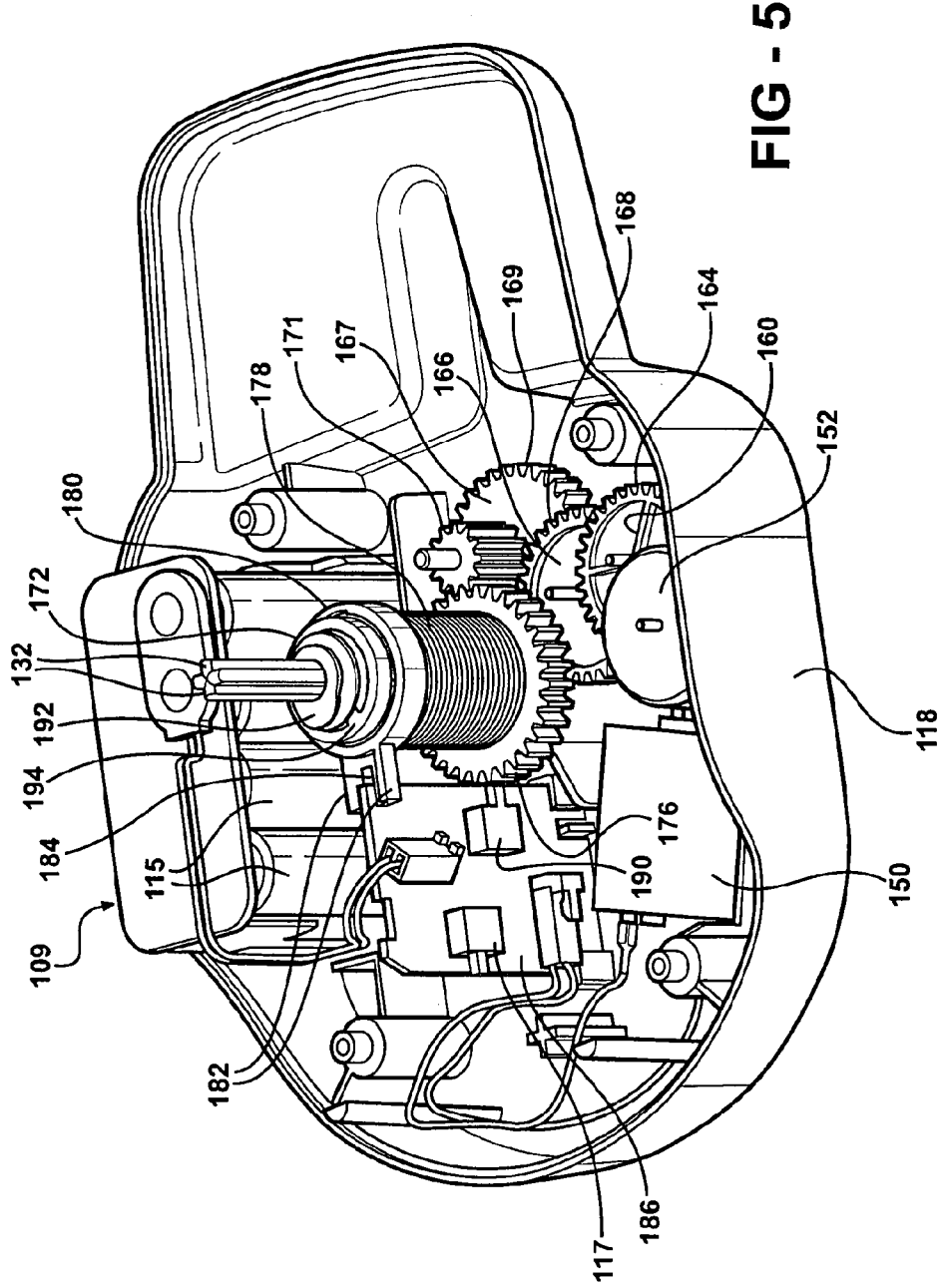
FIG. 5 is a partial top perspective view of a bottom housing portion of the mixer showing a switch and gears of the transfer mechanism.
Figure 16:
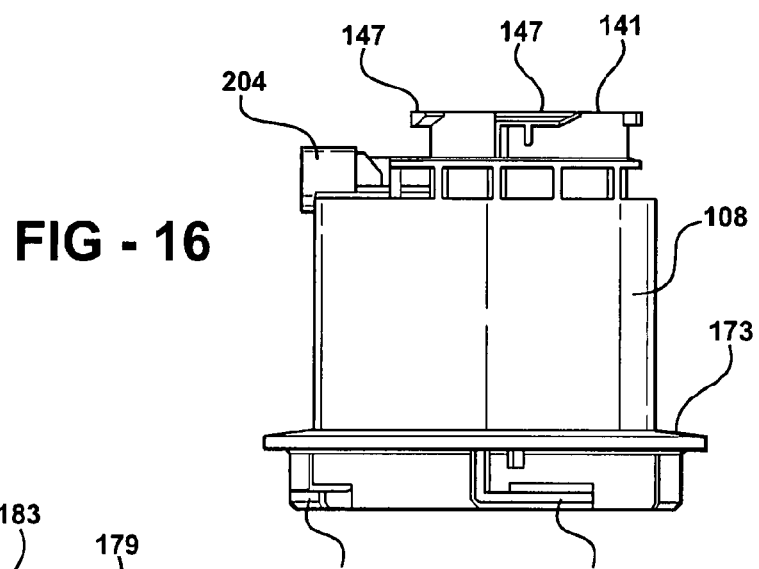
FIG. 16 is a side elevational view of the mixer housing.
Figure 17:
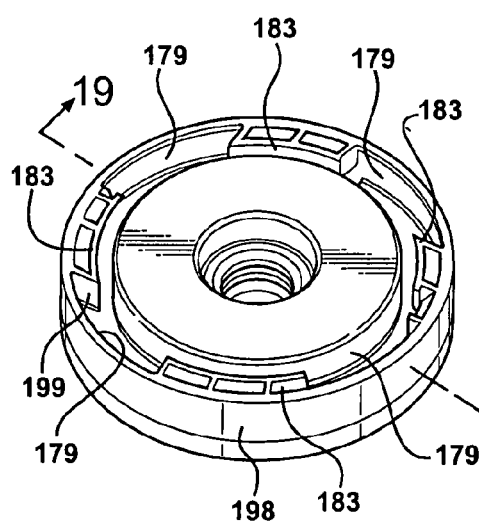
FIG. 17 is a top perspective view of a transfer disc of the mixer.
Figure 18:
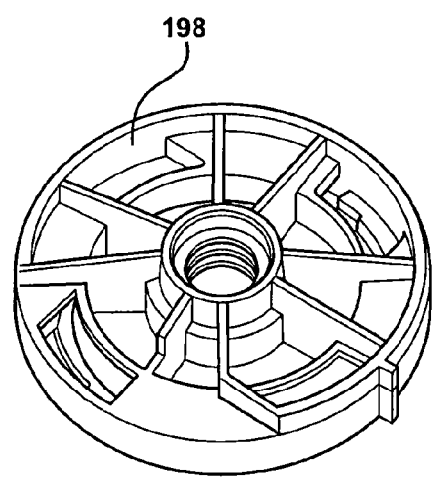
FIG. 18 is a bottom perspective view of the transfer disc.
Figure 19:
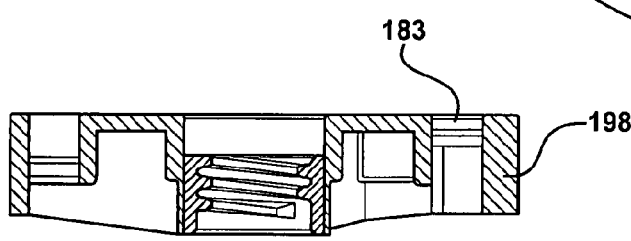
FIG. 19 is a cross-sectional view of the transfer disc taken generally along the line 19-19 in FIG. 17.

Referring to FIGS. 4 and 5, the mixer 102 is shown with the casing 107 removed to expose some of its internal components. As shown, the mixer 102 is battery-powered. Batteries 115 are used to power a motor 150 that drives the mixing and transfer operations of the mixer 102. In one embodiment, a battery pack 109 of eight batteries 115 is used to power the motor 150. The motor 150 is preferably a reversible DC motor such as those available from Mabuchi Motor Co. of Matsudo City, Japan. Possible models that could be used include Model Nos. RC-280RA-2865 and RC-280SA-2865. The mixer 102 is preferably disposable such that the motor 150 and batteries 115 are selected for single use. A switch 117 closes a circuit (see FIG. 49) between the batteries 115 and the motor 150 to begin operation of the motor 150. The switch button 114, when pressed, trips the switch 117 to close the circuit. Once the mixing and transfer operations are complete, the motor 150 ceases to operate.

Referring to FIGS. 6 and 7, the base 106 of the mixer 102 comprises a bottom housing portion 118 and a middle housing portion 116 secured to the bottom housing portion 118 using conventional fasteners, adhesives, and the like. A mixing shaft 120 is rotatably supported between the housing portions 116, 118. The mixing shaft 120 has a mixing gear 122 with mixing gear teeth 123 at one end. The mixing shaft 120 is rotatably supported in the bottom housing portion 118 by a centering pin 119. The mixing shaft 120 extends from the mixing gear end to a second end 124 that is connected to a mixing paddle 126. This connection is preferably releasable, but could include integral or fixed connections.

Referring to FIGS. 6-10, the mixing paddle 126 includes a hub 128 with inner splines 130 that interact with outer splines 132 on the mixing shaft 120 to rotationally lock the mixing shaft 120 to the mixing paddle 126 during the mixing phase (shown in FIGS. 8 and 10). The outer splines 132 extend along the entire length of the mixing shaft 120 from the mixing gear 122. This rotational locking feature allows the mixing shaft 120 to impart rotational motion to the mixing paddle 126 to adequately mix the bone cement components. When mixing is complete, the rotational lock between the mixing shaft 120 and the hub 128 is removed to prevent further rotation of the mixing paddle 126 in the transfer phase.

The preferred embodiment of the mixing paddle 126 is shown in FIGS. 9A, 9B, and 10. In one embodiment, the mixing paddle 126 is formed of injection molded plastic. In other embodiments, the mixing paddle 126 is formed from a flat piece of plastic or metal material. In these embodiments, the mixing paddle 126 is cut from the flat piece of material and folded/shaped to the configuration shown in FIG. 9A. The mixing paddle 126 includes a flat base section 222 and a bent flap 220 forming an obtuse angle with the flat base section 222. The flat base section 222 is fixed to the hub 128 by being integrally molded with the hub 128 or by adhesive or the like. The hub 128 extends downwardly from the flat base section 222. The bent flap 220 is radially spaced from a center of the hub 128. As the mixing paddle 126 rotates, the bent flap 220 urges the bone cement components upwardly. A pair of flat arms 224 extends upwardly from the flat base section 222 generally perpendicularly to the flat base section 222. The flat arms 224 act as mixing vanes to mix the bone cement components.

A flat connector section 226 extends between and connects the flat arms 224. The flat connector section 226 forms an obtuse angle A with the flat arms 224. As a result, when the mixing paddle 126 is urged upwardly in the mixing chamber 138 during the transfer phase (further described below), the flat connector section 226 strikes a top of the mixer housing 108. As the mixing paddle 126 continues to move upwardly in the mixing chamber 138, the mixing paddle 126 begins to compress toward a flattened configuration. This includes bending the flat arms 224 downward toward the flat base section 222 about a hinge, then eventually flattening the flat connection section 226 and the bent flap 220 such that they all fall in generally the same plane as the flat base section 222 (see FIG. 9B).

Referring to FIGS. 6-7 and 11-13, a piston 134 supports the mixing paddle 126. More specifically, the hub 128 of the mixing paddle 126 is seated in a bore 136 defined through the piston 134. An O-ring (not illustrated) seals the hub 128 in the bore 136. The piston 134 is releasably secured in the mixer housing 108. A second O-ring (not identified) seals the piston 134 to an interior surface of the mixer housing 108. The piston 134 includes a pair of flexible tabs 135 that rest beneath a shoulder 137 defined in the interior surface of the mixer housing 108. The flexible tabs 135 hold the piston 134 in place until such time as the piston 134 is forced upwardly to transfer the mixture to the delivery device 104 in the transfer phase. At that point, the flexible tabs 135 are forced inwardly to allow the piston 134 to move upwardly along the interior surface of the mixer housing 108. In the mixing phase, however, the piston 134 remains in place and forms a mixing chamber 138 with the mixer housing 108.

In one embodiment, the mixer 102 may be shipped with a powder component of the bone cement stored in the mixing chamber 138. In this embodiment, a cap 140 is releasably coupled to the mixer housing 108 during shipment to keep the powder component in the mixing chamber 138. More specifically, the cap 140 is secured to a cylindrically-shaped top port 141 of the mixer housing 108.

The top port 141 defines a pour opening 143 (see FIG. 14) that enters the mixing chamber 138 through a plurality of web sections 145 that form a web. A plurality of port flanges 147 extends radially outwardly from the top port 141 to engage the cap 140. The cap 140 includes a plurality of locking tabs 149 that engage the port flanges 147 to lock the cap 140 to the mixer housing 108. An o-ring seals the cap 140 to the mixer housing 108. When the system 100 is ready to be used, the user removes the cap 140 to add a liquid component of the bone cement through the pour opening 143 to the powder component already placed in the mixing chamber 138 or also added through the pour opening 143. Once the components are disposed in the mixing chamber 138, the mixer 102 is ready for operation.

The motor 150 operates through a gear arrangement to rotate the mixing shaft 120 during the mixing phase to mix the powder and liquid components. Rotation of the mixing shaft 120 imparts rotation to the mixing paddle 126, which is disposed in the mixing chamber 138. The gear arrangement includes a face gear 152 having a set of face gear teeth 154. A pinion gear 156 (see FIG. 22) is fixed to a shaft of the motor 150 to rotate with the motor 150 during operation. The pinion gear 156 has pinion gear teeth 157 engaging the face gear teeth 154 such that the motor 150 drives the face gear 152 during operation.

The face gear 152 drives a first spur gear 160, which drives a second spur gear 166. More specifically, the face gear 152 has a lower set of gear teeth 154 continuously engaging an upper set of spur gear teeth 162 formed on the first spur gear 160. A lower set of spur gear teeth 164 formed on the first spur gear 160 continuously engages an upper set of spur gear teeth 168 formed on the second spur gear 166. The upper set of spur gear teeth 168 engages the mixing gear teeth 123 to rotate the mixing shaft 120 and mixing paddle 126 during the mixing phase.

The second spur gear 166 drives a third spur gear 167. In particular, a lower set of spur gear teeth 170 formed on the second spur gear 166 engages a lower set of spur gear teeth 169 formed on the third spur gear 167. The third spur gear 167 also includes an upper set of spur gear teeth 171 (see FIG. 7). The upper set of spur gear teeth 171 formed on the third spur gear 167 engages a set of transfer gear teeth 176 formed on a transfer gear 172. As a result, when the motor 150 operates, both the mixing shaft 120 and the transfer gear 172 rotate. Each of the face gear 152 and spur gears 160, 166, 167 are supported by centering pins captured between the middle housing portion 116 and the bottom housing portion 118.

The transfer gear 172 is generally cylindrical and includes a first open end and a second, partially closed, end defining an aperture. The mixing shaft 120 is rotatably supported in the aperture such that rotation of the mixing shaft 120 does not interfere with rotation of the transfer gear 172. The speed with which the mixing shaft 120 and transfer gear 172 rotate depends on the gear ratios of the gears. In some embodiments, the gear ratios are set such that the transfer gear 172 rotates slower than the mixing shaft 120.

The transfer gear 172 forms part of a transfer mechanism of the mixer 102. The transfer mechanism transfers the mixture out from the mixing chamber 138 and into a delivery chamber of the delivery device 104 after mixing. Transfer threads 178 are defined on an outer surface of the transfer gear 172. A switch nut 180 is threaded on the outer surface of the transfer gear 172. The switch nut 180 is fixed from rotation so that as the transfer gear 172 rotates, the switch nut 180 moves along the outer surface of the transfer gear 172. The switch nut 180 has two projections 182 with a notch 184 defined therebetween. The notch 184 rides along an edge of a printed circuit board 186 fixed to the bottom housing 118 to prevent rotation of the switch nut 180 with the transfer gear 172. In other words, the edge of the printed circuit board 186 rides in the notch 184 between the projections 182 as the transfer gear 172 rotates thereby preventing the switch nut 180 from rotating. The motor 150, by way of its rotation of the transfer gear 172, operatively engages the switch nut 180. This is best shown in FIG. 5.

During operation, after the switch 117 has been closed, the switch nut 180 rides along the printed circuit board 186 as it further threads onto the transfer gear 172 in one direction until it engages a second switch 190 (see FIG. 5), spaced from the switch 117. Thus, the switch nut 180 acts as a switch actuator 180. Other suitable actuators could be employed. The second switch 190, when tripped by movement of the switch nut 180, opens the circuit between the batteries 115 and the motor 150 to shut down operation of the motor 150 (see FIG. 49).

The transfer mechanism further includes a driver 192 that is keyed to the transfer gear 172 to rotate with the transfer gear 172. Thus, the transfer gear 172 operatively couples the motor 150 to the driver 192. The driver 192 includes keyways 193 (see FIG. 22), while the transfer gear 172 includes keys 195 (see FIG. 22) slidably disposed in the keyways 193. In other embodiments, the driver 192 could include the keys 195, while the transfer gear 172 includes the keyways 193. Of course, other coupling mechanisms could be used to lock rotation of the transfer gear 172 to the driver 192. The driver 192 is free to move axially relative to the transfer gear 172. The driver 192 has driving threads 194 defined on its outer surface. During the mixing phase, the driving threads 194 are rotatably received in a bore 196 of a transfer disc 198. The transfer disc 198 is coupled to a bottom of the mixer housing 108 and fixed from movement. The transfer disc 198 also forms part of the transfer mechanism and acts as a drive nut for the driver 192.

During the mixing phase, the driving threads 194 rotate within the bore 196 of the transfer disc 198 and engage corresponding threads 202 in the bore 196. Thus, the transfer disc 198 operates as a fixed drive nut. FIGS. 6 and 7 show the driving threads 194 fully advanced through the bore 196. This represents the end of the mixing phase. A spring 203 biases the driver 192 upwardly in the cavity of the transfer gear 172 to facilitate engagement with the threads 202. The time required for the driving threads 194 to fully advance through the bore 196 represents the mixing phase. In other words, a predetermined mixing period is set by the amount of time it takes for the driving threads 194 to fully advance through the transfer disc 198. Once the driving threads 194 completely pass through the bore 196, the transfer phase begins. The transfer phase continues for a predetermined transfer period, which is defined between the start of transfer and the actuation of the second switch 190, which ceases operation of the motor 150.

Figure 20:
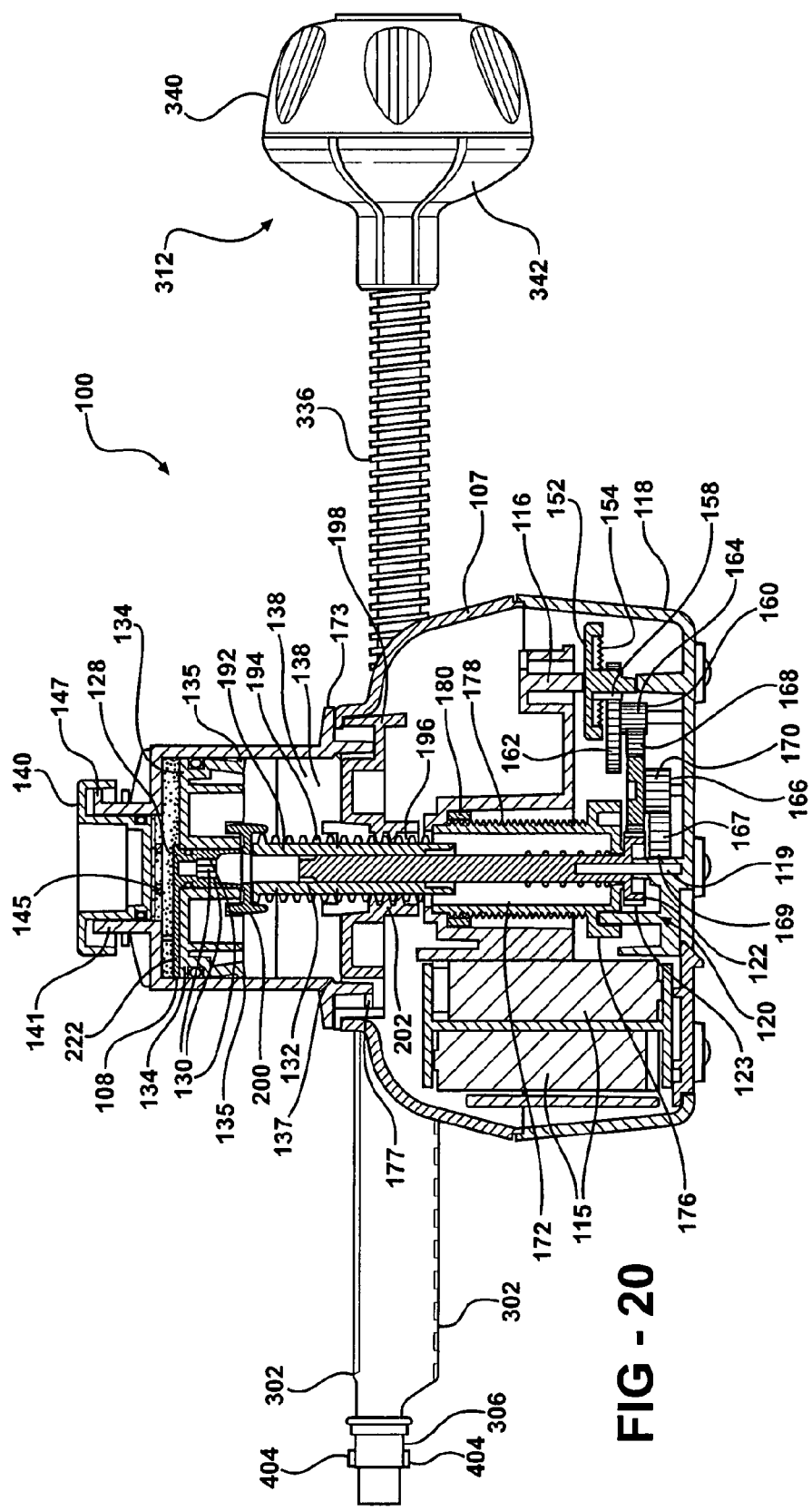
FIG. 20 is a cross-sectional view of the system of FIG. 1 in a transfer phase.
Figure 21:
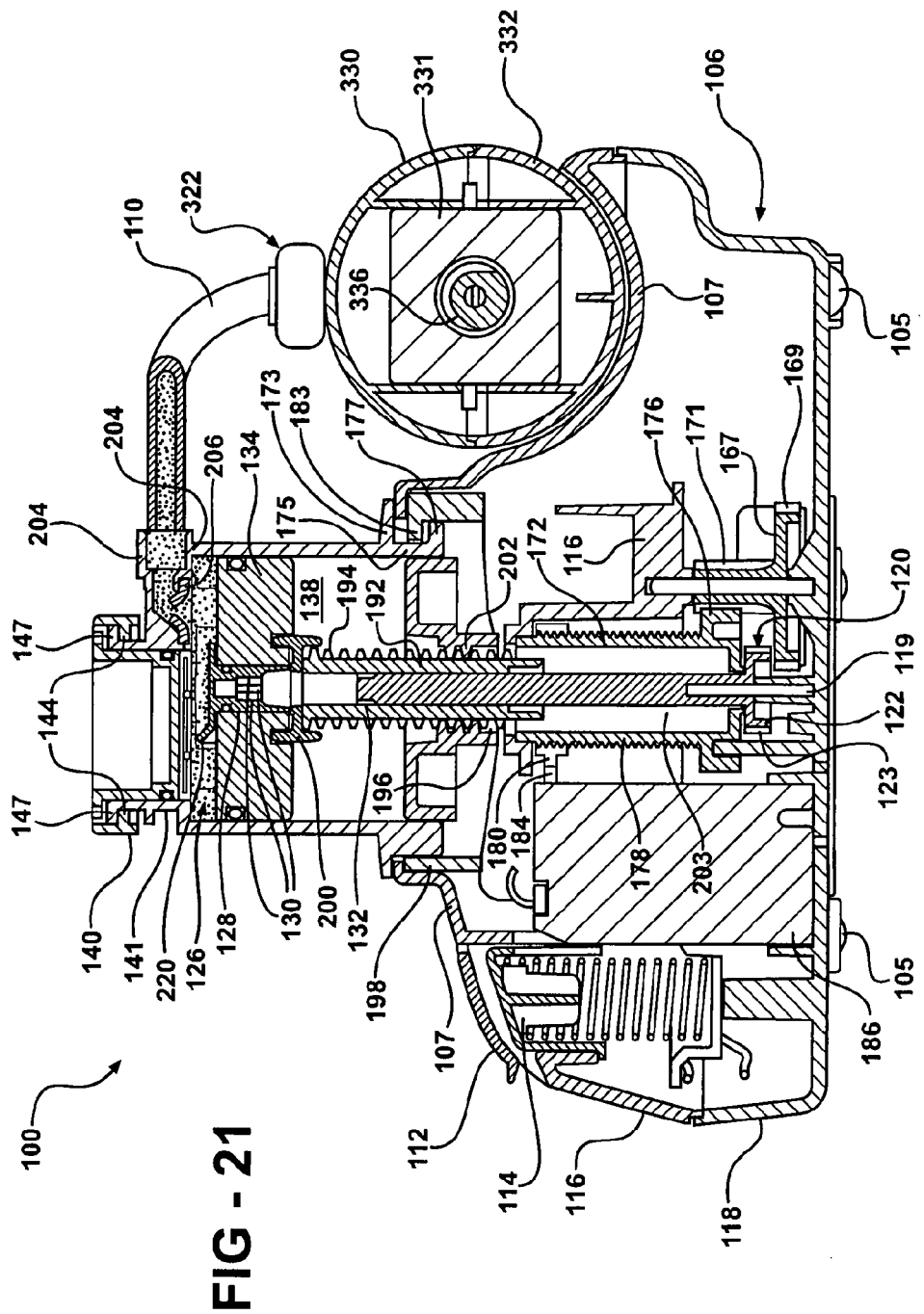
FIG. 21 is another cross-sectional view of the system of FIG. 1 in the transfer phase.

Referring to FIGS. 20 and 21, when the driver 192 advances in the transfer phase, it pushes the push cap 200 axially upwardly against the piston 134, which in turn urges the piston 134 upwardly to move through the mixing chamber 138. The piston 134 is sealed to the wall of the mixer housing 108 and includes a face that contacts the mixture in the mixing chamber 138. The mixture is pushed upwardly through an exit port 204 (also referred to as a transfer port 204; see FIG. 21) into the transfer conduit 110 and then into the delivery device 104. For this reason, the piston 134 is also considered part of the transfer mechanism of the mixer 102.

As the driver 192 advances in the transfer phase and moves the piston 134 through the mixing chamber 138, the driver 192/piston 134 disengages the mixing paddle 126 from the mixing shaft 120. More specifically, the hub 128 with inner splines 130 is lifted off the outer splines 132 on the mixing shaft 120 to rotationally unlock the mixing shaft 120 from the mixing paddle 126 during the transfer phase. The mixing shaft 120 is held down by the transfer gear 172 while the mixing paddle 126 is disengaged from the mixing shaft 120. As the piston 134 rises in the mixing chamber 138, the mixing paddle 126 folds down to a compact size to permit a majority of the mixture to be pressed out of the mixing chamber 138 and into the delivery device 104.

The motor 150 operates through the gear arrangement to rotate the mixing shaft 120 and actuate the mixing paddle 126 during the mixing phase to mix the powder and liquid components, while also rotating the transfer gear 172 to actuate the transfer mechanism to automatically transfer the mixture from the mixing chamber 138 to the delivery chamber of the delivery device 104 after the predetermined mixing period has elapsed. In other words, the motor 150 operatively engages both the mixing shaft 120 and the transfer mechanism (including the transfer gear 172, driver 192, piston 134, etc.). The motor 150 continues operation from its start, upon actuation of the switch 117, until it stops upon actuation of the second switch 190, during which time the motor 150 operates to mix the components in the mixer 102 and transfer the mixture to the delivery device 104. In one embodiment, the switch 117 and the second switch 190 are combined into a single switch (not shown) that is closed to start operation of the motor 150 by an actuator, and opened to stop operation of the motor 150.

In still other embodiments, the second switch 190 reverses the polarity of the motor 150 and causes the transfer gear 172 to reverse its rotation. Consequently, the switch nut 180 changes direction and rides back along the printed circuit board 186. In this embodiment, the threads 202 are configured such that during the mixing phase the driving threads 194 cannot engage the threads 202 of the transfer disc 198. However, when the polarity switch 190 is tripped by the switch nut 180, the driver 192 reverses its direction of rotation with the transfer gear 172 and engages the threads 202 in a manner that advances the driver 192 axially during the transfer phase. In this embodiment, a third switch (not shown) or other mechanism would be required to be tripped by the switch nut 180 as it travels back along the printed circuit board 186 to stop operation of the motor 150.

As shown in FIGS. 7 and 14-19, the bottom of the mixer housing 108 includes a flange 173 and a short wall 175 extending downwardly from the flange 173. A plurality of locking tabs 177 (see FIG. 15) are spaced circumferentially about the short wall 175 and extend radially outwardly from the short wall 175. During assembly of the mixer 102, the locking tabs 177 are inserted into openings 179 (see FIG. 17) defined in a top of the transfer disc 198. The casing 107 is captured between the mixer housing 108 and the transfer disc 198 when this is done (see FIG. 21). The mixer housing 108 is then rotated one-quarter turn such that the locking tabs 177 slide beneath corresponding locking members 183 on the transfer disc 198 until they reach stops 199. The piston 134 rests on top of the transfer disc 198 and is initially coupled to the transfer disc 198 by the push cap 200.

Figure 22:
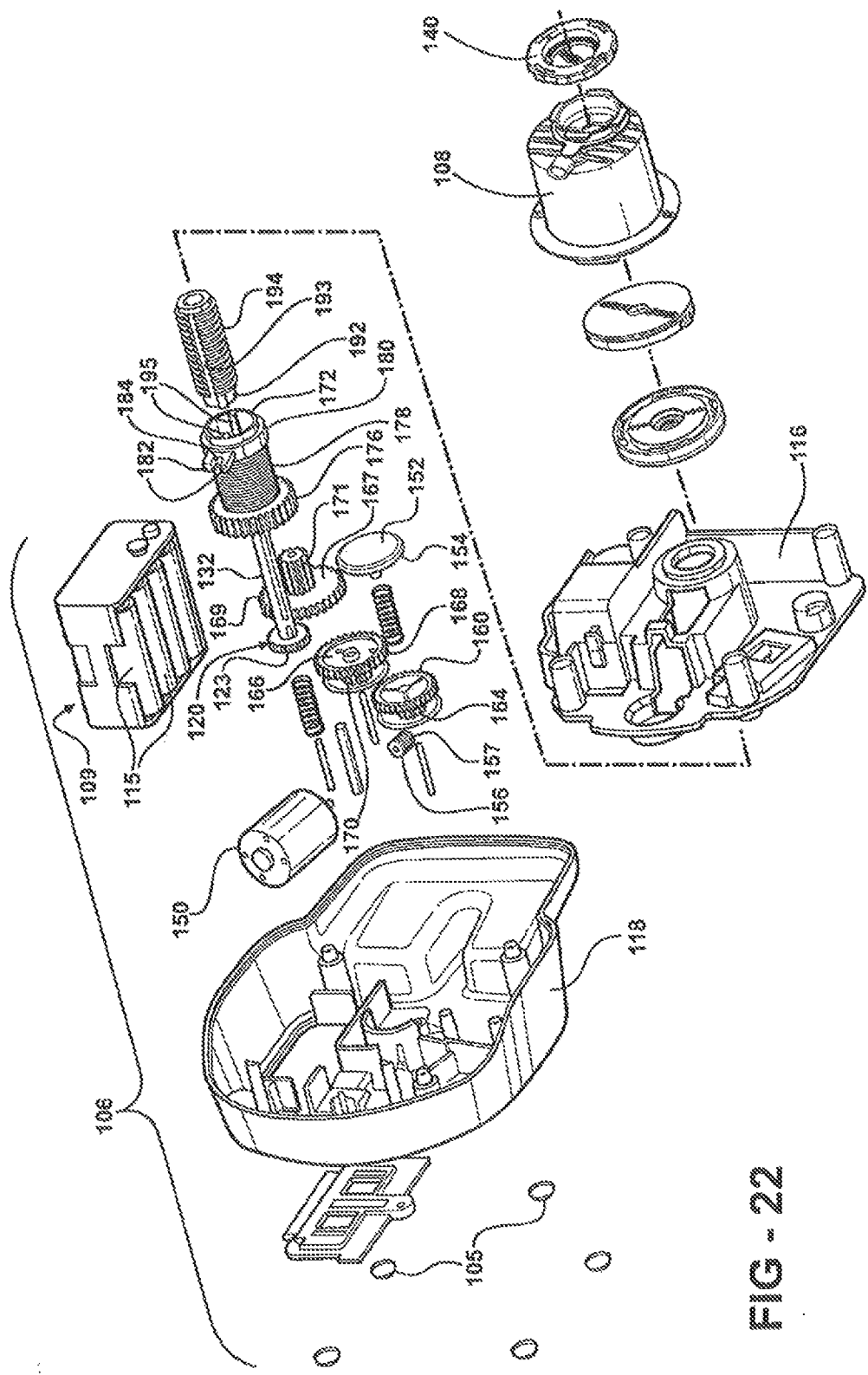
FIG. 22 is an exploded view of a base of the mixer.

FIG. 22 illustrates an exploded view of the base 106 including the bottom housing portion 118, the middle housing portion 116, and the gear arrangement disposed therebetween for converting motor operation into mixing and transfer operations. FIG. 23 shows the base 106 fully assembled.

FIGS. 24-29 illustrate perspective views of the transfer gear 172, the driver 192, the switch nut 180, the first spur gear 160, the second spur gear 166, and the third spur gear 167.

Referring to FIGS. 30-32, the cap 140 is shown. The cap 140 includes a top 232. A cap wall 234 is disposed on the top 232 and extends downwardly from the top 232 to a bottom wall 236. A gripping flange 238 extends downwardly from the top 232 and is spaced from the cap wall 234. A plurality of locking tabs 240 are disposed on the gripping flange 238 and extend radially inwardly into a gap between the gripping flange 238 and the cap wall 234. The locking tabs 240 engage the tabs 147 on the top port 141.

Referring to FIGS. 7, 33, and 34, a valve 206 is arranged in the exit port 204 to prevent the escape of unmixed components during mixing. Referring to FIG. 34, the valve includes a plastic or metal ring 210 having a plurality of apertures 212 for receiving an elastomeric material 213 in a molding process. The material 213 fills in the apertures 212 as shown in FIG. 34 and includes cross-cut slits 214 that remain closed in the mixing phase, but open up and allow the mixture to flow therethrough into the transfer conduit 110 during the transfer phase.

II. Alternative Mixing Paddles

Alternative embodiments of the mixing paddle 126 are shown in FIGS. 35A-38B. In FIGS. 35A and 35B, the mixing paddle 126' is formed of plastic and includes a pair of flat arms 224' extending upwardly from a flat base section 222'. A pair of opposed bent flaps 220' form an obtuse angle with the flat base section 222'. In this embodiment, the flat arms 224' are opposed from one another on opposite sides of a center of the mixing paddle 126'. The flat arms 224' further include bent ends 225' that strike the top of the mixer housing 208 in the transfer phase and bend inwardly to flatten the flat arms 224'.

Referring to FIGS. 36A and 36B, the mixing paddle 126' is formed of metal such as stainless steel or aluminum.

In FIGS. 37A and 37B, a mixing paddle 126" has a pair of opposed arms 224" that are pivotally connected to a flat base section 222" by a pair of pivot pins 229.

In FIGS. 38A and 38B, a mixing paddle 126''' includes a flat base section 222''', a bent flap 220''' forming an obtuse angle with the flat base section 222''', and a single flat arm 224''' extending upwardly generally perpendicularly to the flat base section 222'''. An extension 231 extends at an obtuse angle for crossing the mixing chamber 138. In each of the embodiments of the alternative mixing paddles, the arms 224', 224", 224''' are configured to be supported by the wall of the mixer housing 108 during rotation in the clockwise direction (when viewed from above), but unsupported when rotating in the counterclockwise direction. When unsupported, they are urged into their compressed state. This is useful when the motor 150 changes direction during the transfer phase, as described in the alternative transfer embodiment above.

The mixer housing 108, transfer disc 198, mixing shaft 120, transfer gear 172, face gear 152, spur gears 160, 166, 167, switch nut 180, driver 192, piston 134, cap 140, mixing paddle 126, bottom housing portion 118, middle housing portion 116, casing 107, and switch cover 112 are preferably formed of a bio-compatible plastic material such as nylon, PBT (polybutylene terephthalate), PC (polycarbonate), ABS (acrylonitrile butadiene styrene), glass-filled nylon, glass-filled polyetherimide, or the like.

III. Delivery Device

Referring to FIGS. 39-42, the delivery device 104 is shown. The delivery device 104 comprises a reservoir 302 defining the delivery chamber for receiving the bone cement mixture from the transfer conduit 110 during the transfer phase. The reservoir 302 includes an entry port 314 (or inlet port 314) defined in a sidewall of the reservoir 302. A valve housing 316 (see also FIG. 42) is outfitted with an o-ring 318 and is seated in the entry port 314. The valve housing includes a plurality of flow paths 319 and a central bore 321. As shown in FIG. 41, a one-way umbrella valve 320 is supported in the central bore 321 of the valve housing 316 such that the bone cement mixture opens the valve 320 to fill the reservoir 302. The one-way umbrella valve 320 prevents the bone cement mixture from re-entering the mixer 102 during the transfer phase. A handle 304 is mounted about the reservoir 302 for grasping by the user.

A rotatable fitting 322 is secured in the valve housing 316 during the mixing and delivery phases. To accomplish this, the rotatable fitting 322 fits through an aperture 325 in the handle 304. The rotatably fitting 322 includes a pair of diametrically opposed locking tabs 306 that engages the handle 304. The handle 304 includes a plurality of locking flanges 327 spaced circumferentially from one another in the aperture 325. The locking flanges 327 extend radially inwardly into the aperture 325. During assembly, the locking tabs 306 pass into the aperture 325 between the locking flanges 327 and are rotated into place with the locking tabs 306 disposed beneath the locking flanges 327. An annular flange 329 of the rotatable fitting 322 rests on top of the locking flanges 327 when in position (see FIG. 41).

One end of the transfer conduit 110 fits into the rotatable fitting 322. A through bore 331 is defined through the rotatable fitting 322 to transfer the bone cement mixture to the reservoir 302 from the transfer conduit 110. During transfer the bone cement mixture passes through the through bore 331 under pressure thereby opening the one-way umbrella valve 320 and passing through the flow paths 319 (see FIG. 42) into the reservoir 302. Once transfer is complete, the rotatable fitting 322 is rotated counterclockwise to release the rotatable fitting 322 from the valve housing 316 thereby allowing the user to remove the delivery device 104 from its cradle mounts 333 on the mixer 102 in preparation for delivering the bone cement mixture to the target site.

A nut 324 is mounted to a proximal end of the reservoir 302. In particular, the proximal end of the reservoir 302 has a rectangular flange 326 for supporting the nut 324. The rectangular flange 326 slides into a slot 328 defined in the nut 324. The nut 324 has a generally box-like shape that is secured between two halves 330, 332 of the handle 304. Each half 330, 332 of the handle 304 has a complimentary box-shaped cavity 334 such that the nut 324 fits snugly in the cavities 334 when the halves 330, 332 are fixed together. The halves 330, 332 may be fixed together by conventional fasteners, adhesives, and the like.

Figure 40:
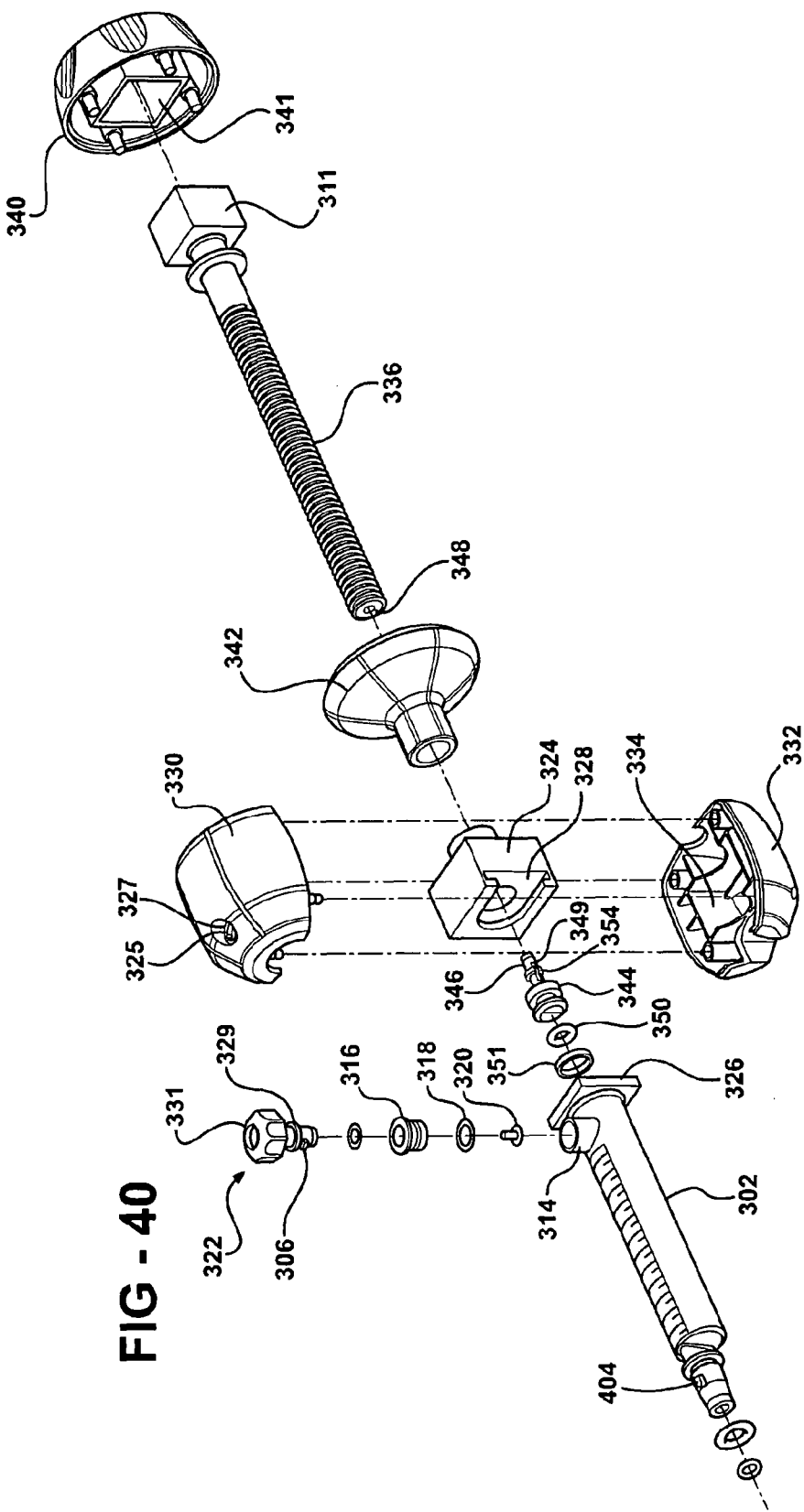
FIG. 40 is an exploded perspective view of the delivery device.

A plunger 310 drives the mixture through the delivery chamber of the reservoir 302 during delivery. The plunger 310 includes a threaded shaft 336 that engages threads 338 of the nut 324. A plunger head 344 is snap-fit to the threaded shaft 336 to form a distal end of the plunger 310. The plunger head 344 is snap-fit to the threaded shaft 336 by inserting a stem 346 of the plunger head 344 into a bore 348 defined through the threaded shaft 336. Referring to FIGS. 40 and 41, the stem 346 has a pair of diametrically opposed detent ramps 354 that slide through the bore 348 in a compressed configuration (by being pressed together via a slot 349 defined through the stem 346) until the ramps 354 pass a shoulder 356 in the bore 348. Once they pass the shoulder 356, the ramps 354 spring outwardly to engage the shoulder 356 and prevent withdrawal of the plunger head 344. An o-ring 350 is seated with a dynamic seal 351 in an outer groove defined in the plunger head 344 to seal against an interior of the reservoir 302.

A proximal end 311 of the plunger 310 has a generally box-like shape. A knob 312 is mounted about the proximal end 311 of the plunger 310 to facilitate rotation of the plunger 310. The knob 312 has a proximal knob portion 340 defining a box-shaped cavity 341 for receiving the proximal end 311 of the plunger 310 such that as the user rotates the proximal knob portion 340, the plunger 310 also rotates. A distal knob portion 342 is fastened to the proximal knob portion 340 using fasteners, adhesives, or the like. The proximal end 311 of the plunger 310 is captured between the proximal 340 and distal 342 knob portions to prevent the proximal end 311 of the plunger 310 from slipping out of the box-shaped cavity 341.

IV. Alternative Delivery Device with Clutch

Figure 43:
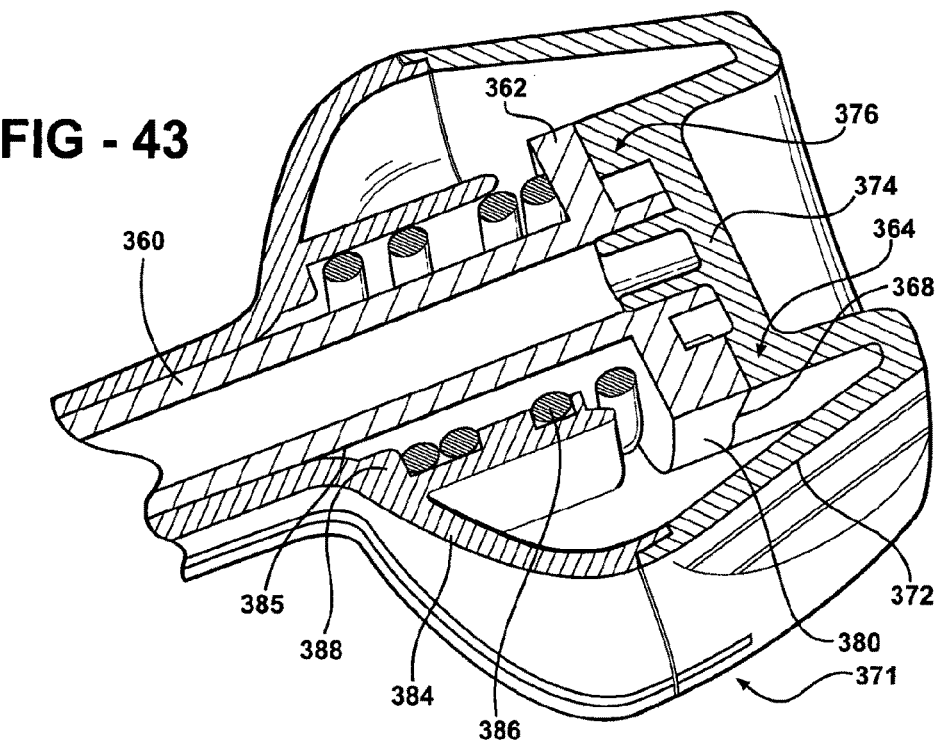
FIG. 43 is a partial cross-sectional perspective view illustrating an optional clutch mechanism of the delivery device.
Figure 44:
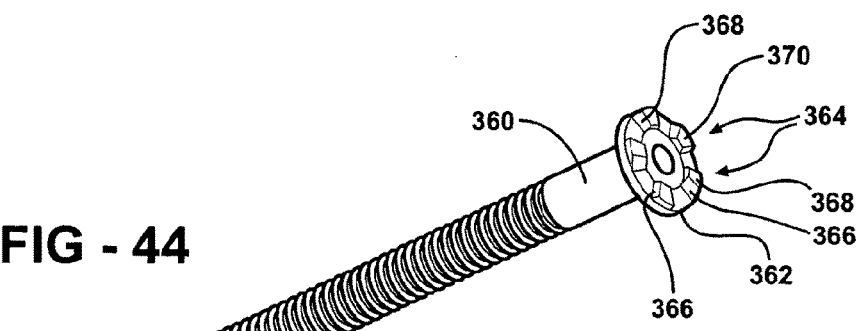
FIG. 44 is a top perspective view of an alternative plunger of the delivery device.
Figure 45:
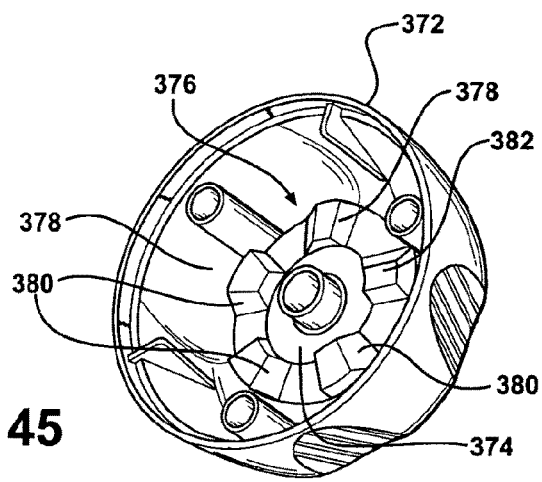
FIG. 45 is a bottom perspective view of an alternative proximal knob portion of the delivery device.

Referring to FIGS. 43-45, an alternative plunger shaft 360 is shown. Referring specifically to FIG. 44, a proximal end of the plunger shaft 360 includes a flange 362 and a plurality of projections 364 disposed on the flange 362. The plurality of projections 364 extend proximally from the flange 362. The projections 364 are circumferentially spaced from one another about a periphery of the flange 362. Each of the projections 364 has a vertical surface 366 and an angled surface 368 (forms acute angle with flange 362) meeting at a plateau 370 generally parallel to the flange 362. In the embodiment, a knob 371 is mounted to the proximal end of the plunger shaft 360 to facilitate rotation of the plunger shaft 360. The knob 371 includes a proximal knob portion 372. The proximal knob portion 372 includes a top 374 and a plurality of complimentary projections 376 disposed on the top 374 and extending distally from the top 374. The complimentary projections 376 mate with the projections 364 on the flange 362 by fitting in spaces defined between the projections 364 on the flange 362.

Each of the complimentary projections 376 also includes a vertical surface 378 and an angled surface 380 meeting at a plateau 382 generally parallel to the top 374. A distal knob portion 384 is fastened to the proximal knob portion 372 using fasteners, adhesives, or the like. The proximal end of the plunger shaft 360 is captured between the proximal 372 and distal 384 knob portions. The plunger shaft 360 passes through a bore 385 defined through the distal knob portion 384. A spring 386 rests on a shoulder 388 defined in the distal knob portion 384 about the bore 385. The spring 386 acts between the shoulder 388 and the flange 362.

The spring 386, along with the projections 364, 376, form a clutch mechanism. This clutch mechanism can be configured to slip when undesired pressures are reached in the delivery device 104. During use, when a user is rotating the knob 371, the projections 376 formed on the proximal knob portion 372 engage the projections 364 formed on the flange 362 of the plunger shaft 360. In particular, the angled surfaces 368, 380 engage one another as the user rotates the knob 371 clockwise. The spring 386 acts to keep the angled surfaces 368, 380 in engagement during normal operation. However, when undesired pressures are reached the angled surfaces 368, 380 begin to slip and the flange 362 separates from the proximal knob portion 372. As a result, the projections 364, 376 slide out of engagement thereby preventing further advancement of the plunger shaft 360 until pressure is normalized. Different spring constants can be used to alter the pressure at which the clutch mechanism is actuated. Furthermore, the projections 364, 376 could be oriented radially, as opposed to axially, such that axial forces supplied by the user does not affect the clutch mechanism's operation.

V. Extension Tube with Enlarged Connector

Referring to FIG. 46, an extension tube 400 is shown mounted to the distal end of the reservoir 302. In one embodiment, the extension tube 400 is automatically primed with bone cement during the transfer phase. In other words, the system 100 is designed for use with specified mixture volumes that fill both the reservoir 302 and the extension tube 400 in the transfer phase. This eliminates the need for the user to prime the extension tube 400 manually.

Referring to FIGS. 47 and 48, the extension tube 400 includes a tube fitting 402 for securing the extension tube 400 to the delivery port 306 of the reservoir 302. Referring back to FIG. 39, the delivery port 306 includes a pair of diametrically opposed projections 404 and the tube fitting 402 includes a pair of diametrically opposed channels 406 for receiving the projections 404 when the tube fitting 402 is axially mounted onto the discharge port 306. Once the projections 404 bottom-out in the channels 406, the tube fitting 402 is rotated. The projections 404 then ride in diametrically opposed slots 408 defined through the tube fitting 402. The tube fitting 402 is then prevented from axially sliding off the delivery port 306. In other embodiments, the tube fitting 402 is fixed to the delivery port 306 with adhesive, press fit, welding, or the like.

Referring to FIG. 47, an enlarged luer-lock connector 410 is mounted to a distal end of the extension tube 400. The luer-lock connector 410 comprises a knob 412, a spindle 414, and a collar 416. The collar 416 includes a side port 418 defining a side bore 426. A main bore 420 is defined through the collar 416 normal to the side port 418. The distal end of the extension tube 400 fits into the side bore 426 of the side port 418. The extension tube 400 may be fixed in the side port 418 by press fit, ultrasonic welding, adhesive, or the like.

The spindle 414 is rotatably supported in the main bore 420 of the collar 416. A pair of o-rings 415 seals the spindle 414 in the main bore 420. The spindle 414 includes a through bore 422 and a cross bore 424 aligned with the side bore 426 in the side port 418. The cross bore 424 is disposed between the o-rings 415. The knob 412 includes a stem 428 that fits into the through bore 422 in a top of the spindle 414. The stem 428 is fixed in the through bore 422 by a press-fit, ultrasonic welding, adhesive, or the like.

The knob 412 further includes a grasping portion 430 shaped for grasping by a hand of the user. The spindle 414 fits inside an annular cavity 432 in the knob 412. A bottom of the spindle 414 has a connector portion 434, e.g., the threaded female portion of a standard luer-lock fitting 434. The through bore 422 continues through the luer-lock fitting 434. As seen in FIG. 47, the luer-lock fitting 434 is located outside of one end of the collar 416 and has an outer surface that is located inwardly of the outer perimeter of the collar. The luer-lock fitting 434 is configured for attachment to the complementary threaded male portion of a luer-lock fitting 436 on a delivery cannula 440. During use, the user grasps the grasping portion 430 of the knob 412 and rotates the knob 412 and spindle 414 to lock the luer-lock fitting 434 of the spindle 414 on the luer-lock fitting 436 on the delivery cannula 440. The oversized grasping portion 430 facilitates easier connection of the extension tube 400 to the delivery cannula 440 to deliver the bone cement mixture through the extension tube 400, the through bore 422, the delivery cannula 440, and to the target site.

The reservoir 302, rotatable fitting 322, handle 304, knob 312, plunger 310, nut 324, valve housing 316, tube fitting 402, and enlarged luer-lock connector 410 are preferably formed of a bio-compatible plastic material such as nylon, PBT (polybutylene terephthalate), PC (polycarbonate), ABS (acrylonitrile butadiene styrene), glass-filled nylon, glass-filled polyetherimide, or the like. The umbrella valve 320 is preferably formed of nitrile.

VI. Alternative Delivery Device with Delivery Motor

Figure 51:
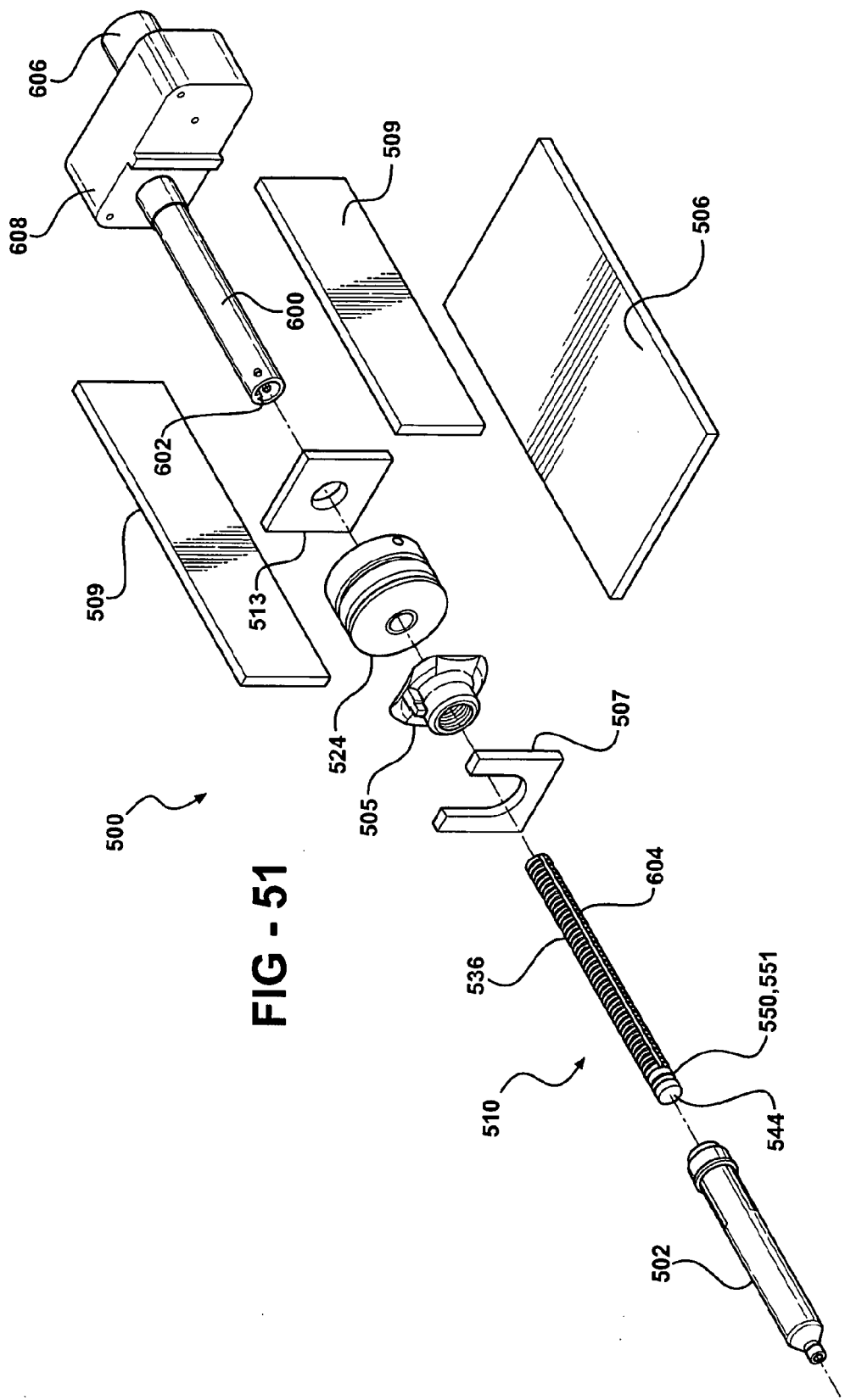
FIG. 51 is an exploded view of the motorized delivery device.
Figure 52:
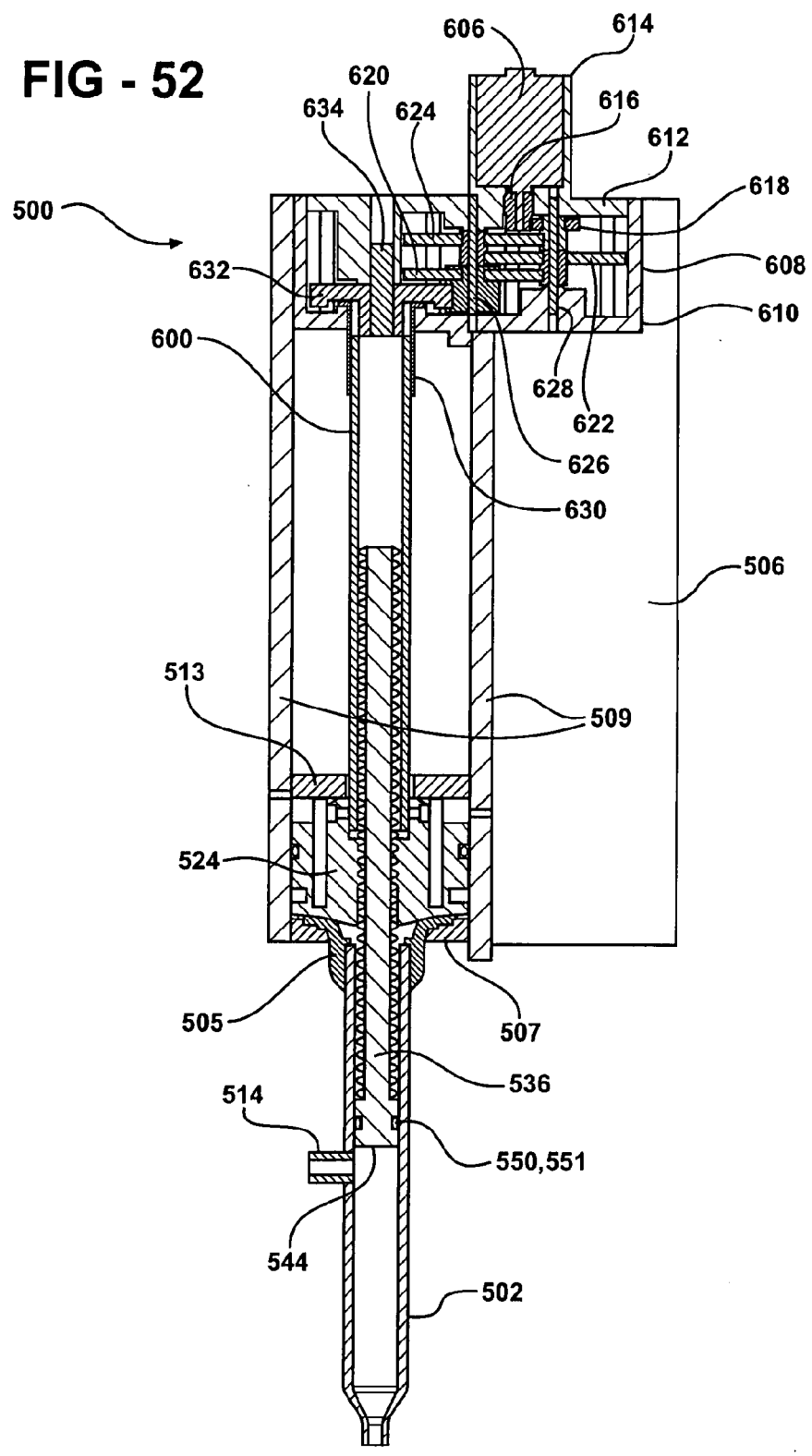
FIG. 52 is a cross-sectional view of the motorized delivery device.

Referring to FIGS. 50-52, an alternative delivery device 504 is shown. The delivery device 500 comprises a reservoir 502 defining a delivery chamber for receiving the bone cement mixture from the transfer conduit 110 during the transfer phase. The reservoir 502 threadably engages a cap 505 seated in an end plate 507. The end plate 507 is supported between and fixed to two side plates 509. The end plate 507 has a U-shaped cutout portion into which the cap 505 extends. The cutout portion supports the cap 505. A bottom plate 506 supports and is fixed to the side plates 509. A middle plate 513 is fixed to the bottom plate 506 and the two side plates 509. The middle plate 513 is preferably rectangular in shape to prevent rotation of the middle plate 513 between the side plates 509. A nut 524 is disposed between the middle plate 513 and the cap 505. The nut 524 is fixed from rotation relative to the plates 507, 509, 513 by being fixed to the middle plate 513 by adhesive, welding, fasteners, or the like.

Referring to FIGS. 51 and 52, a plunger 510 drives the mixture through the delivery chamber of the reservoir 502 during delivery. The plunger 510 includes a threaded shaft 536 that engages threads (not shown) of the nut 524. A plunger head 544 is fixed to the threaded shaft 536 to form a distal end of the plunger 510. An o-ring 550 with a dynamic seal 551 is seated in an outer groove defined in the plunger head 544 to seal against an interior of the reservoir 502.

A proximal end 511 of the plunger 510 is slidably disposed in a rotating drive shaft 600. The drive shaft 600 is hollow and includes a key 602 disposed along its internal surface. The key 602 protrudes radially inwardly. The plunger 510 includes a keyway 604 disposed in an outer surface of the threaded shaft 536. The key 602 is configured to slide in the keyway 604 as the drive shaft 600 rotates due the fixed nature of the nut 524.

Referring to FIG. 52, a delivery motor 606 and gear box 608 operate to rotate the drive shaft 600. The gear box 608 includes a box 610 and a cover 612. The delivery motor 606 is supported in a mounting sleeve 614 disposed on the cover 612. A motor shaft 616 penetrates through the cover 612 into the gear box 608. A pinion gear 616 is fixed to the motor shaft 616 to rotate with the delivery motor 606 during its operation. A series of spur gears 618, 620, 622, 624 are rotatably supported by shafts 626, 628. The shafts 626, 628 are fixed to the box 610 and cover 612 for support.

A proximal end of the drive shaft 600 is rotatably supported in the box 610 by a bushing 630. A drive gear 632 is fixed to the proximal end of the drive shaft 600 and rotatably supported by a shaft 634. The shaft 634 is fixed to the cover 612. The series of spur gears 618, 620, 622, 624 transfer power from the motor shaft 616 to the drive gear 632 during operation. A switch 640 controls operation of the delivery motor 606. The delivery motor 606 may be powered by a battery pack 607. After the mixture has been transferred from the mixing chamber 138 to the delivery chamber of the reservoir 502, as described above, the user can operate the delivery motor 606 to deliver the mixture to the target site.

VII. Drool Valve and Viscosity Meter

Referring back to FIG. 50, a drool valve 700 may be positioned at any point along the extension tube 400, including at the distal end of the extension tube 400. The drool valve 700 may be a motor-controlled valve or a solenoid valve. The drool valve 700 is controlled by a controller 702. The controller 702, in this embodiment, also controls the delivery motor 606 through the switch 640. The drool valve 700 operates to discontinue flow of the mixture through the extension tube 400 from the delivery device 500 upon actuation of the delivery switch 640 thereby preventing excess mixture from entering the target site. Without the drool valve 700, when the user actuates the delivery switch 640 to stop operation of the delivery motor 606, there is still pressure in the extension tube 400 due to the compressible nature of the mixture. This pressure tends to deliver an additional amount of the mixture to the target site after the user desires to stop flow of the mixture. With the drool valve 700, the amount of the mixture delivered can be better controlled.

In operation, the user actuates the switch 640 to send power to the drool valve 700 and the delivery motor 606. This opens the drool valve 700 and starts operation of the delivery motor 606. Operation of the delivery motor 606 rotates the drive shaft 600 and advances the plunger 510 in the reservoir 502 to begin delivering the mixture from the reservoir 502, down the extension tube 400, to the target site. When the user wishes to stop the flow of the mixture, the switch 640 is again actuated to signal the controller 702 that the delivery motor 606 is to be stopped and the drool valve 700 is to be closed. The controller 702 then discontinues power to the delivery motor 606 and the drool valve 700.

A viscosity meter 710 monitors current draw on the delivery motor 606 to approximate the viscosity of the mixture in the reservoir 502. The viscosity meter 710 can be a current meter integrated into the controller 702 to monitor the current draw from the delivery motor 606. The controller 702 then correlates current draw to viscosity by way of a look-up table using correlation values that can be easily derived. A display 712 then displays the approximate viscosity of the mixture. Of course, the viscosity measurement is an estimate and not an exact measurement of viscosity, but can be useful in determining how much longer the working time window for the particular bone cement being used will remain open.

While this description is directed to a few particular embodiments, it is understood that those skilled in the art may conceive of modifications and/or variations to the specific embodiments shown and described herein. Any such modifications or variations that fall within the purview of this description are intended to be included herein as well. It is understood that the description herein is intended to be illustrative only and is not intended to be limited.

What is claimed is:

1. A device for injecting bone cement into bone, said device including:

a reservoir tube, said reservoir tube having opposed proximal and distal ends, said reservoir tube having a void space located between the ends for holding bone cement;

a plunger moveably mounted to said reservoir tube adjacent the proximal end of said reservoir tube, said plunger mounted to said reservoir tube so as to be selectively advanced towards the distal end of said reservoir tube in order to force bone cement out of the distal end of said reservoir tube;

an extension tube mounted to the distal end of said reservoir tube so as to extend forward of said reservoir tube and to receive the bone cement forced out of said reservoir tube, said extension tube having an open distal end;

a collar mounted to the distal end of said extension tube to receive the bone cement; and a connector, said connector including:

a fitting located adjacent a first end of said collar, said fitting formed with threading;

a spindle that extends through said collar, said spindle being rotatably mounted in said collar and being connected to said fitting to rotate said fitting, wherein said collar, said fitting and said spindle are collectively shaped so that bone cement discharged from said extension tube can flow out of said fitting; and a knob attached to said spindle so as to be located adjacent a second end of said collar opposite the first end, said knob being connected to said spindle so as to rotate said spindle and said connector fitting; and a cannula, said cannula configured for insertion into living tissue, said cannula having a cannula fitting configured to engage with and disengage from said connector fitting upon rotation of said connector fitting.

2. The device for injecting bone cement of claim 1, wherein said spindle is formed with at least one bore that defines a fluid communications path from said extension tube to said connector fitting.

3. The device for injecting bone cement of claim 1, further including:

a shell separate from said reservoir tube, said shell defining a mixing chamber for receiving bone cement-forming components, said shell being in fluid communication with the reservoir tube;

a paddle movably disposed in the shell mixing chamber for mixing the bone cement-forming components into bone cement; and a piston disposed in said shell adjacent said paddle and having a face directed towards the shell mixing chamber, said piston being moveably mounted to said shell to move through the mixing chamber so as to push the bone cement out through said shell into said reservoir tube.

4. The device for injecting bone cement of claim 3, further including a connecting tube that extends between said shell and said reservoir tube, said connecting tube defining a fluid communications path between said shell and said reservoir tube.

5. The device for injecting bone cement of claim 3, wherein said paddle is collapsible within the shell mixing chamber.

6. The device for injecting bone cement of claim 1, wherein said knob projects outwardly from said collar.

7. The device for injecting bone cement of claim 1, wherein said connector fitting and said connector spindle are formed as a single piece component.

8. The device for injecting bone cement of claim 1, wherein:
said connector fitting and said connector spindle are formed as a single piece component; and
said connector knob is separate from and secured to said connector spindle so as to form a single component with said connector spindle and said connector fitting.

9. A device for injecting bone cement into bone, said device including:
a reservoir tube, said reservoir tube having opposed proximal and distal ends, said reservoir tube having a void space located between the ends for holding bone cement;
a plunger moveably mounted to said reservoir tube adjacent the proximal end of said reservoir tube, said plunger mounted to said reservoir tube so as to be selectively advanced towards the distal end of said reservoir tube in order to force bone cement out of the distal end of said reservoir tube;
an extension tube mounted to the distal end of said reservoir tube so as to extend forward of said reservoir tube and further to receive the bone cement forced out of the reservoir tube, said extension tube having an open distal end;
a collar mounted to the distal end of said extension tube to receive the bone cement; and
a connector, said connector including:
a fitting located adjacent and outside of a first end of said collar, said fitting having an outer surface that is located inwardly of an outer perimeter of said collar and said fitting being formed with threading;
a spindle that extends through said collar, said spindle being rotatably mounted in said collar and being connected to said fitting to rotate said fitting, wherein said collar, said fitting and said spindle are collectively shaped so that bone cement discharged from said extension tube can flow out of said fitting; and
a knob attached to said spindle so as to be located adjacent a second end of said collar opposite the first end, said knob extending radially outwardly beyond said collar and being connected to said spindle so as to rotate said spindle and said connector fitting; and
a cannula, said cannula configured for insertion into living tissue, said cannula having a cannula fitting configured to engage with and disengage with said connector fitting upon rotation of said connector fitting.

10. The device for injecting bone cement of claim 9, wherein said spindle is formed with at least one bore that defines a fluid communications path from said extension tube to said connector fitting.

11. The device for injecting bone cement of claim 9, wherein:
said collar is formed with a bore in which said spindle is rotatably mounted and from which said connector fitting extends;
said spindle is formed with: an axially extending bore that opens into said connector fitting and an inlet bore that extend into the axially extending bore, the inlet bore providing a fluid communication path between said extension tube and said spindle axially extending bore; and
at least one seal extends around said spindle so as to be located between said spindle and an interior surface of said collar that defines the collar bore, said at least one seal being located between the spindle inlet bore and said knob or between the spindle inlet bore and said connector fitting.

12. The device for injecting bone cement of claim 9, further including:
a shell separate from said reservoir tube, said shell defining a mixing chamber for receiving bone-cement forming components, said shell being in fluid communication with said reservoir tube;
a paddle movably disposed in the shell mixing chamber for mixing the bone cement-forming components into bone cement; and
a piston disposed in said shell adjacent said paddle and having a face directed towards the shell mixing chamber, said piston being moveable mounted to said shell to move through the mixing chamber so as to push the cement out through said shell into said reservoir tube.

13. The device for injecting bone cement of claim 12, further including a connecting tube that extends between said shell and said reservoir tube, said connecting tube defining a fluid communications path between said shell and said reservoir tube.

14. The device for injecting bone cement of claim 9, wherein:
said connector fitting and said connector spindle are formed as a single piece component; and
said connector knob is separate from and secured to said connector spindle so as to form a single component with said connector spindle and said connector fitting.

15. A device for injecting bone cement into bone, said device including:
a reservoir tube, said reservoir tube having opposed proximal and distal ends, said reservoir tube having a void space located between the ends for holding bone cement;
a plunger moveably mounted to said reservoir tube adjacent the proximal end of the reservoir tube, said plunger mounted to said reservoir tube so as to be selectively advanced towards the distal end of said reservoir tube in order to force bone cement out of the distal end of said reservoir tube;
an extension tube mounted to the distal end of said reservoir tube so as to extend forward of said reservoir tube and further to receive the bone cement forced out of said reservoir tube, said extension tube having an open distal end;
a collar mounted to the distal end of said extension tube to receive the bone cement, said collar having first and second opposed ends; and
a connector, said connector including
a fitting located adjacent and outside of the first end of said collar, said fitting having an outer surface that is located inwardly of an outer perimeter of said collar and said fitting being formed with threading;
a spindle that extends through said collar, said spindle being rotatably mounted in said collar and being connected to said connector fitting to rotate said connector fitting, wherein said spindle has at least one bore that establishes a fluid communications path from the distal end of said extension tube to said connector fitting; and
a knob attached to said spindle so as to be located adjacent the second of end of said collar, said knob being connected to said spindle so as to rotate said spindle and said connector fitting; and
a cannula, said cannula configured for insertion into living tissue, said cannula having a cannula fitting configured to engage with and disengage with said connector fitting upon rotation of said connector fitting.

16. The device for injecting bone cement of claim 15, wherein:
   said collar is formed with a bore in which said spindle is rotatably mounted;
   said spindle is formed with: an axially extending bore that opens into said connector fitting and an inlet bore that extends from the axially extending bore, the inlet bore providing a fluid communications path between said extension tube and said spindle axially extending bore; and
   at least one seal extends around said spindle so as to be located between said spindle and an interior surface of said collar that defines the collar bore, said at least one seal being located between the spindle inlet bore and said knob or between the spindle inlet bore and said connector fitting.

17. The device for injecting bone cement of claim 15, further including:
   a shell separate from said reservoir tube, said shell defining a mixing chamber for receiving bone-cement forming components, the shell being in fluid communication with said reservoir tube;
   a paddle movably disposed in the shell mixing chamber for mixing the bone cement-forming components into bone cement; and
   a piston disposed in said shell adjacent said paddle and having a face directed towards the shell mixing chamber, said piston being moveably mounted to said shell to move through the mixing chamber so as to push the bone cement out through the shell into said reservoir tube.

18. The device for injecting bone cement of claim 17, wherein said paddle is collapsible within the shell mixing chamber.

19. The device for injecting bone cement of claim 15, wherein said connector fitting and said connector spindle are formed as a single piece component.

20. The device for injecting bone cement of claim 15, wherein said connector spindle and said connector knob are separate components that are secured together to form a unitary assembly.

* * * * *